(12) United States Patent
Saito

(10) Patent No.: US 10,045,719 B2
(45) Date of Patent: Aug. 14, 2018

(54) ENDOSCOPE SYSTEM, PROCESSOR DEVICE THEREOF, AND METHOD FOR DISPLAYING OXYGEN SATURATION LEVEL

(71) Applicant: FUJIFILM Corporation, Tokyo (JP)

(72) Inventor: Takaaki Saito, Ashigarakami-gun (JP)

(73) Assignee: FUJIFILM Corporation, Tokyo (JP)

(*) Notice: Subject to any disclaimer, the term of this patent is extended or adjusted under 35 U.S.C. 154(b) by 511 days.

(21) Appl. No.: 13/658,590

(22) Filed: Oct. 23, 2012

(65) Prior Publication Data

US 2013/0113906 A1 May 9, 2013

(30) Foreign Application Priority Data

Nov. 9, 2011 (JP) ................................ 2011-245600

(51) Int. Cl.
*A61B 1/04* (2006.01)
*A61B 5/145* (2006.01)
(Continued)

(52) U.S. Cl.
CPC .......... *A61B 5/145* (2013.01); *A61B 1/00009* (2013.01); *A61B 1/04* (2013.01);
(Continued)

(58) Field of Classification Search
CPC ..... A61B 1/00009; A61B 1/0646; A61B 1/05; A61B 1/042; A61B 5/145; A61B 5/1459;
(Continued)

(56) References Cited

U.S. PATENT DOCUMENTS 5,078,150 A * 1/1992 Hara et al. ..................... 600/476
5,956,416 A * 9/1999 Tsuruoka ............ G06F 19/3406
348/65

(Continued)

FOREIGN PATENT DOCUMENTS

JP         3-21186 A     1/1991
JP     2001-218217 A     8/2001
(Continued)

OTHER PUBLICATIONS

Japanese Office Action, dated Feb. 26, 2014, for Japanese Application No. 2011-245600 is provided, as well as an English translation.

(Continued)

*Primary Examiner* — Jessica M Prince
*Assistant Examiner* — Kathleen Nguyen
(74) *Attorney, Agent, or Firm* — Birch, Stewart, Kolasch & Birch, LLP

(57) ABSTRACT

In a special mode, an internal body portion is imaged under a first white light beam to obtain a first frame composed of blue, green, and red signals. Sequentially, the body portion is imaged under a second white light beam to obtain a second frame composed of blue, green, and red signals. An oxygen saturation level is calculated from the signals. A special image is produced based on the oxygen saturation level. A displacement between the first and second frames is calculated from the signals. If the displacement is a first allowable value or more and less than a second allowable value, the special image is displayed with a lower chroma on a monitor, as compared with a case where the displacement is less than the first allowable value. If the displacement is the second allowable value or more, the special image is converted into a gray scale image.

11 Claims, 17 Drawing Sheets

(51) Int. Cl.
  *A61B 1/00* (2006.01)
  *A61B 1/06* (2006.01)
  *A61B 5/00* (2006.01)
  *A61B 5/1455* (2006.01)
  *A61B 5/1459* (2006.01)
  *G06T 7/00* (2017.01)
  *G06T 7/246* (2017.01)

(52) U.S. Cl.
  CPC ............ *A61B 1/063* (2013.01); *A61B 1/0638* (2013.01); *A61B 1/0646* (2013.01); *A61B 1/0653* (2013.01); *A61B 1/0669* (2013.01); *A61B 5/0071* (2013.01); *A61B 5/1455* (2013.01); *A61B 5/1459* (2013.01); *G06T 7/0012* (2013.01); *G06T 7/246* (2017.01); *A61B 5/489* (2013.01); *G06T 2207/10016* (2013.01); *G06T 2207/10024* (2013.01); *G06T 2207/10068* (2013.01); *G06T 2207/10152* (2013.01); *G06T 2207/30004* (2013.01)

(58) Field of Classification Search
  CPC ........... A61B 5/489; H04N 2005/2255; H04N 2005/235; H04N 2005/2256
  USPC .......... 348/68; 600/323, 339, 310, 504, 118, 600/101, 477
  See application file for complete search history.

(56) References Cited

U.S. PATENT DOCUMENTS

| | | | |
|---|---|---|---|
| 5,974,338 | A | 10/1999 | Asano et al. |
| 2007/0060798 | A1* | 3/2007 | Krupnik ............. A61B 1/00045 600/300 |
| 2008/0269606 | A1* | 10/2008 | Matsumura .......... A61B 5/0048 600/438 |
| 2010/0056928 | A1* | 3/2010 | Zuzak et al. .................. 600/476 |
| 2010/0310239 | A1* | 12/2010 | Kono ................. A61B 1/00009 386/343 |
| 2011/0040217 | A1* | 2/2011 | Centen ................. A61B 5/0064 601/41 |
| 2011/0237883 | A1 | 9/2011 | Chun |
| 2011/0237884 | A1 | 9/2011 | Saito |

FOREIGN PATENT DOCUMENTS

| | | |
|---|---|---|
| JP | 2002-85344 A | 3/2002 |
| JP | 2011-194151 A | 10/2011 |
| JP | 2476373 A1 | 7/2012 |

OTHER PUBLICATIONS

Japanese Office Action for Japanese Application No. 2011-245600 dated Nov. 20, 2013, with English translation.

European Office Action, dated Feb. 24, 2016, for European Application No. 12190835.4.

EPO communication pursuant to Article 94(3) EPC dated Feb. 17, 2017, for European Application No. 12190835.4.

European Communication Pursuant to Article 94(3) EPC, dated Jan. 17, 2018, for corresponding European Application No. 12190835.4.

* cited by examiner

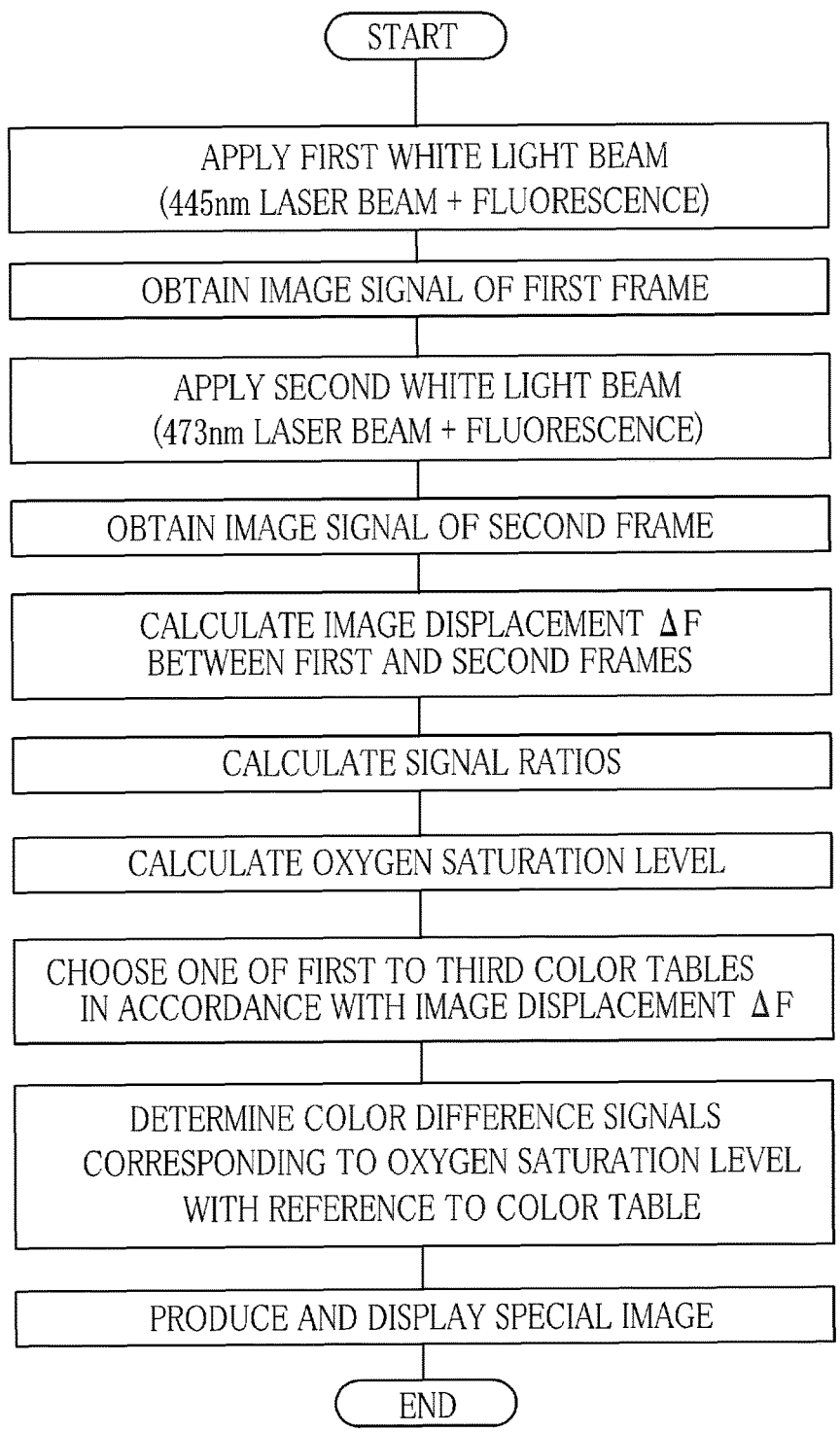

ENDOSCOPE SYSTEM, PROCESSOR DEVICE THEREOF, AND METHOD FOR DISPLAYING OXYGEN SATURATION LEVEL

BACKGROUND OF THE INVENTION

1. Field of the Invention

The present invention relates to an endoscope system having the function of imaging an oxygen saturation level of blood, a processor device of the system, and a method for displaying the oxygen saturation level.

2. Description Related to the Prior Art

Endoscopy is widely available as a minimally invasive diagnostic and treatment procedure. The endoscopy uses an endoscope system that has an electronic endoscope, a light source device, a processor device, and a monitor. Recently, there is known the endoscope system that has not only a normal mode of observing the inside of a body cavity or lumen under white light (normal light), but also a special mode using light (special light) in a specific narrow wavelength band to facilitate finding out a lesion.

In the normal mode, the normal light such as xenon light in a wide wavelength band is applied from the electronic endoscope inserted into the body cavity to an internal body surface, and a color image sensor captures the light reflected from the body surface. A color image obtained by the image sensor is subjected to image processing in the processor device, and is displayed on the monitor. In another technique, as described in Japanese Patent Laid-Open Publication Nos. 2001-218217 and 2002-085344, the normal light is separated into three color light beams of R, G, and B, and the three color light beams are sequentially applied to the internal body surface. The reflected light beams from the body surface are captured by a three frame sequential method to obtain three frame images. Then, the frame images are merged into a single full color image.

In the special mode, a blood vessel pattern obtaining technique is known in which a blood vessel in a specific depth is emphasized using the special light having a wavelength at which hemoglobin has a high light absorption coefficient. Also, as described in U.S. Pat. No. 5,956,416 and US Patent Application Publication No. 2011/237884, there is known an oxygen saturation level obtaining technique. In this technique, a plurality of special light beams that have different wavelengths including a wavelength at which the light absorption coefficient much differs between oxygenated hemoglobin and deoxygenated hemoglobin are sequentially applied to the internal body surface. The reflected light beams therefrom are captured to obtain a plurality of frame images. The oxygen saturation level is calculated from the plurality of frame images. The above techniques facilitate finding out a lesion such as cancer, which is hard to spot under the normal light.

As described above, in image processing or calculation using a plurality of frame images, difference in imaging timing sometimes causes positional displacement among the plurality of frame images in either of the two modes. In the three frame sequential method, the positional displacement among the frame images manifests itself as color displacement in the full color image. The faster the image sensor contained in a head assembly of the electronic endoscope moves, the more likely the positional and color displacement occurs. For this reason, according to the Japanese Patent Laid-Open Publication No. 2001-218217, if the color displacement caused by the positional displacement among the frame images is beyond an allowable range, a portion of the displacement is masked to visually indicate that the portion has low reliability of the oxygen saturation level. In the US Patent Application Publication No. 2011/237884, registration among the frame images is carried out with respect to the position of a blood vessel to eliminate the positional displacement.

According to the Japanese Patent Laid-Open Publication No. 2002-085344, when the three color freeze frame images of R, G, and B are stored to a memory in response to a freeze command, a movement amount of the head assembly is calculated from the displacement among the frame images of the same color obtained upon the command and before and after the command, and the registration among the three frame images is performed based on the movement amount. Similarly, according to the U.S. Pat. No. 5,956,416, in the correction of the positional displacement among the color frame images of R, G, and B, the frame images of the same color obtained upon the command and before and after the command are converted into binary images. The freeze frame images are made in register based on displacement in a barycenter among the binary images, to eliminate the color displacement in the full color image.

In several years, expectations on diagnosis using the oxygen saturation level of blood are rising. This is because diagnosis using the blood vessel pattern requires a doctor to have adequate knowledge about the blood vessel pattern specific to the cancer, but in the diagnosis using the oxygen saturation level, a hypoxic region being a sign of the cancer is artificially colored on the monitor. Therefore, since the doctor can grasp the lesion at the sight of the monitor, much experience and knowledge are not required of the doctor as compared with the diagnosis using the blood vessel pattern.

In the diagnosis using the oxygen saturation level, the hypoxic region and a hyperoxic region surrounding the hypoxic region are defined as the lesion, so it is required to clearly display a boundary between the hypoxic region and the hyperoxic region by accurately calculating the oxygen saturation level. Thus, it is desirable to calculate the oxygen saturation level with high accuracy. If the calculation accuracy deteriorates due to the positional displacement among the frame images caused by difference in the imaging timing, it is desired to indicate the deterioration in the calculation accuracy. In the Japanese Patent Laid-Open Publication No. 2001-218217, the portion of the color displacement is masked as an invalid area to visually indicate that the portion has low calculation accuracy. However, even in a valid area having no color displacement, the calculation accuracy may be degraded due to another factor such as blood volume. On the other hand, according to the US Patent Application Publication No. 2011/237884, although the registration among the frame images improves the calculation accuracy of the oxygen saturation level, the calculation accuracy is not indicated on the monitor. Even if the image registration is performed inadequately, a calculation result with low accuracy is displayed on the monitor without any notice.

SUMMARY OF THE INVENTION

An object of the present invention is to provide an endoscope system that calculates an oxygen saturation level of blood with high accuracy and indicates deterioration in the calculation accuracy if it occurs, a processor device of the endoscope system, and a method for displaying the oxygen saturation level.

To achieve the above and other objects, an endoscope system according to the present invention includes a lighting section, an image pickup section, an oxygen saturation level calculator, a special image generator, a monitor, a displacement calculator, and a display form switching section. The lighting section sequentially applies a plurality of illumination light beams having different wavelength bands to an internal body portion. The image pickup section sequentially captures reflected light beams from the internal body portion to obtain a plurality of frames of image signals corresponding to types of the illumination light beams. The oxygen saturation level calculator calculates an oxygen saturation level of blood from the image signals. The special image generator produces a special image that is artificially colored in accordance with the oxygen saturation level. The monitor displays the special image. The displacement calculator calculates a positional displacement in the image signals between the frames. The display form switching section switches a display form of the special image in accordance with the positional displacement.

The displacement calculator may calculate as the positional displacement a displacement of an entire image in the image signals between the frames. The display form switching section may switch the display form of the entirety of the special image in accordance with the positional displacement. In another case, the displacement calculator may divide each image signal into a plurality of areas, and calculate a displacement in the image signals between the frames on an area-by-area basis as the positional displacement. The display form switching section may switch the display form on an area-by-area basis in accordance with the positional displacement.

The display form switching section preferably displays the special image such that an amount of information of the oxygen saturation level is decreased with increase in the positional displacement. It is preferable that the decrease in the amount of information of the oxygen saturation level is decrease in a color property value in the special image. The color property value is preferably chroma.

The endoscope system may further include an image registration unit for performing image registration in the image signals between the frames based on the positional displacement. The displacement calculator may re-calculate the positional displacement in the image signals between the frames after the image registration. The display form switching section may switch the display form of the special image in accordance with the re-calculated positional displacement.

The image pickup section may obtain a first image signal corresponding to a first illumination light beam having a first wavelength range in which a light absorption coefficient varies depending on the oxygen saturation level, a second image signal corresponding to a second illumination light beam having a second wavelength range in which the light absorption coefficient varies depending on blood volume, and a third image signal for standardizing the first and second image signals. The oxygen saturation level calculator may calculate the oxygen saturation level based on the first to third image signals. The first to third wavelength ranges may be within a range between 460 and 700 nm. The first wavelength range may be in a blue wavelength band, and the second wavelength range may be in a red wavelength band.

A processor device of an endoscope system according to the present invention includes a receiving section for receiving the image signals from the image pickup section, an oxygen saturation level calculator for calculating an oxygen saturation level of blood from the image signals, a special image generator for producing a special image, a displacement calculator for calculating a positional displacement in the image signals between the frames, and a display form switching section for switching a display form of the special image on the monitor in accordance with the positional displacement.

A method for displaying an oxygen saturation level includes the steps of sequentially applying a plurality of illumination light beams having different wavelength bands to an internal body portion; sequentially capturing reflected light beams from the internal body portion to obtain a plurality of frames of image signals corresponding to types of the illumination light beams; calculating an oxygen saturation level of blood from the image signals; producing a special image, the special image being artificially colored in accordance with the oxygen saturation level; calculating a positional displacement in the image signals between the frames; and switching a display form of the special image on a monitor in accordance with the positional displacement.

According to the present invention, a plurality of illumination light beams are sequentially applied to the internal body portion. Whenever each illumination light beam is applied, the image signals of the single frame are obtained. Based on the image signals of the several frames, the special image is produced in which the oxygen saturation level of blood flowing through a blood vessel is imaged. In displaying the special image on the monitor, the display form of the oxygen saturation level is switched in accordance with the displacement in the image signals between the frames. Thus, it is possible to notify a user at sight of decrease in the reliability of the oxygen saturation level in a case where the displacement occurs. The oxygen saturation level can be accurately calculated without the influence of the blood volume and the displacement between the frames (the positional displacement in the image).

BRIEF DESCRIPTION OF THE DRAWINGS

For more complete understanding of the present invention, and the advantage thereof, reference is now made to the subsequent descriptions taken in conjunction with the accompanying drawings, in which:

FIG. 13 is a flowchart showing an operation process in the special mode;

DESCRIPTION OF THE PREFERRED EMBODIMENTS

Figure 1:
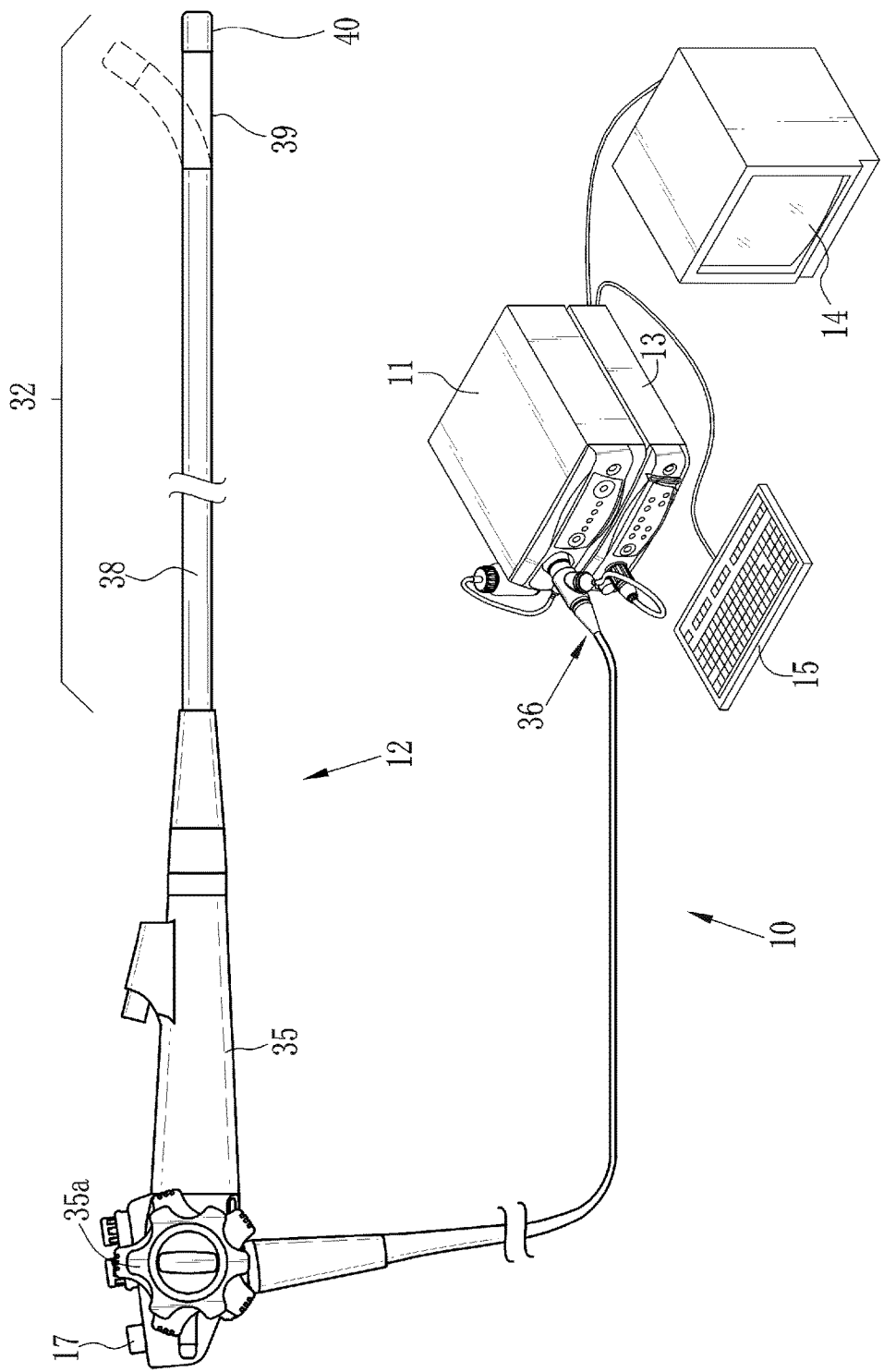
FIG. 1 is a schematic view of an endoscope system according to a first embodiment.

As shown in FIG. 1, an endoscope system 10 according to a first embodiment is constituted of a light source device 11, an electronic endoscope 12, a processor device 13, a monitor 14, and an input device 15 such as a keyboard. The light source device 11 produces light beams in specific wavelength bands. The electronic endoscope 12 leads the light beam from the light source device 11 into a patient's body cavity, and applies the light beam to an internal body portion. The electronic endoscope 12 images the light beam reflected from the body portion, and outputs an image signal. The processor device 13 applies image processing to the image signal to produce an endoscopic image. The endoscopic image is displayed on the monitor 14.

Figure 2:
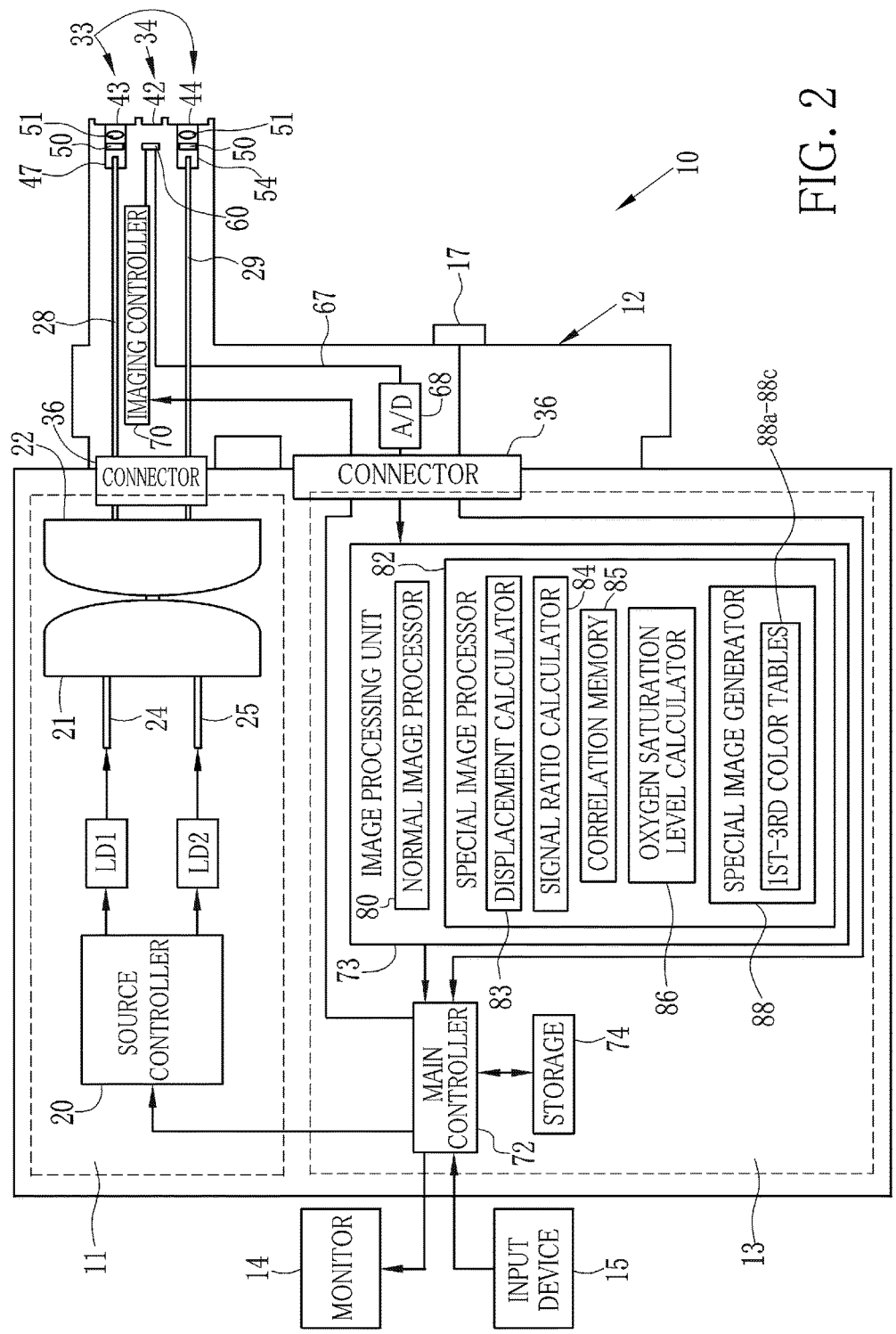
FIG. 2 is a block diagram of the endoscope system.

As shown in FIGS. 1 and 2, the electronic endoscope 12 is provided with a slender insert unit 32 to be introduced into the body cavity, a control handle unit 35 for steering the insert unit 32, and a connector 36 detachably connected to the light source device 11 and the processor device 13.

The insert unit 32 includes a flexible elongated tube 38, a steering assembly 39, and a head assembly 40 provided in this order from the side of the control handle unit 35. The flexible elongated tube 38 flexibly curves in the body cavity. The steering assembly 39 is flexibly bent by a turn of an angle knob 35a provided on the control handle unit 35 so as to aim the head assembly 40 at a desired direction and angle.

Various channels including a forceps channel for inserting a medical instrument and an air/water feed channel extend through the control handle unit 35 and the insert unit 32, though they are not shown.

The endoscope system 10 has a normal mode (normal light observation mode) in which the internal body portion is observed under a white light beam, and a special mode (oxygen saturation level observation mode) in which a plurality of special light beams each having a narrow wavelength band are applied to the internal body portion to calculate an oxygen saturation level of blood. Input from a mode switch 17 provided in the electronic endoscope 12 or input from the input device 15 switches between the normal and the special mode.

As shown in FIG. 2, the light source device 11 includes two laser sources LD1 and LD2 and a source controller 20. The laser source LD1 emits a first laser beam having a center wavelength of 445 nm, while the laser source LD2 emits a second laser beam having a center wavelength of 473 nm. The first and second laser beams excite a phosphor 50, and produce first and second white light beams (pseudo white light beams), respectively. Note that, the first laser beam is preferably in a wavelength range of 440 to 460 nm, and the second laser beam is preferably in a wavelength range of 460 to 480 nm.

The first and second laser beams emitted from the laser sources LD1 and LD2 are incident upon optical fibers 24 and 25, respectively, through a condenser lens (not shown). As the laser source LD1 or LD2, a broad-area type InGaN laser diode, InGaNAs laser diode, GaNAs laser diode, or the like is available.

The source controller 20 controls emission timing of the laser sources LD1 and LD2. In this embodiment, in the normal mode, the laser source LD1 is turned on, while the laser source LD2 is turned off. In the special mode, the laser sources LD1 and LD2 are alternately turned on and off on a frame-by-frame basis. More specifically, when the laser source LD1 is turned on, the laser source LD2 is turned off. When the laser source LD1 is turned off, the laser source LD2 is turned on.

A combiner 21 combines the laser beams from the optical fibers 24 and 25. The combined beam is branched in two beams by a coupler 22 being an optical demultiplexer. The branched two beams are transmitted through light guides 28 and 29, respectively. Each light guide 28, 29 is made of a bundle of a number of optical fibers. Note that, the laser beam from each laser source LD1, LD2 may directly enter the light guides 28 and 29 without through the combiner 21 and the coupler 22.

The head assembly 40 is provided with a lighting section 33 for applying the two illumination light beams transmitted through the light guides 28 and 29 to the internal body portion, and an image pickup section 34 for imaging the internal body portion. The image pickup section 34 includes an imaging window 42 disposed approximately at the center of the head assembly 40. The light beams reflected from the internal body portion pass through the imaging window 42. The lighting section 33 includes two lighting windows 43 and 44 disposed on both sides of the image pickup section 34. The illumination light beams are applied from the lighting windows 43 and 44, i.e. from two directions to the internal body portion.

The lighting windows 43 and 44 contain light projection unit 47 and 54, respectively, in their recess. Each light projection unit 47, 54 makes the first or second laser beam transmitted through the light guides 28 and 29 enter the phosphor 50 to produce the first or second white light beams.

The first or second white light beam is applied to the internal body portion through a lens 51.

The phosphor 50 is made of a plurality of types of fluorescent substances (for example, YAG-based fluorescent substance or BAM ($BaMgAl_{10}O_{17}$)-based fluorescent substance) that are excited by the first or second laser beam from the laser source LD1 or LD2 and emit green to red fluorescence. The entrance of the first or second laser beam into the phosphor 50 produces the pseudo white light beam by mixing of the green to yellow fluorescence emitted from the phosphor 50 and the first or second laser beam passed through the phosphor 50 without being absorbed. Note that, the wavelength of the fluorescence produced from the phosphor 50 slightly varies in accordance with the wavelength of excitation light.

The phosphor 50 preferably has an approximately rectangular parallelepiped shape. The phosphor 50 may be formed by compacting the fluorescent substances by a binder into the rectangular parallelepiped shape. The mixture of resin such as inorganic glass and the fluorescent substance may be formed into the rectangular parallelepiped shape. This phosphor 50 is known under the trademark of Micro White (MW).

Figure 3:
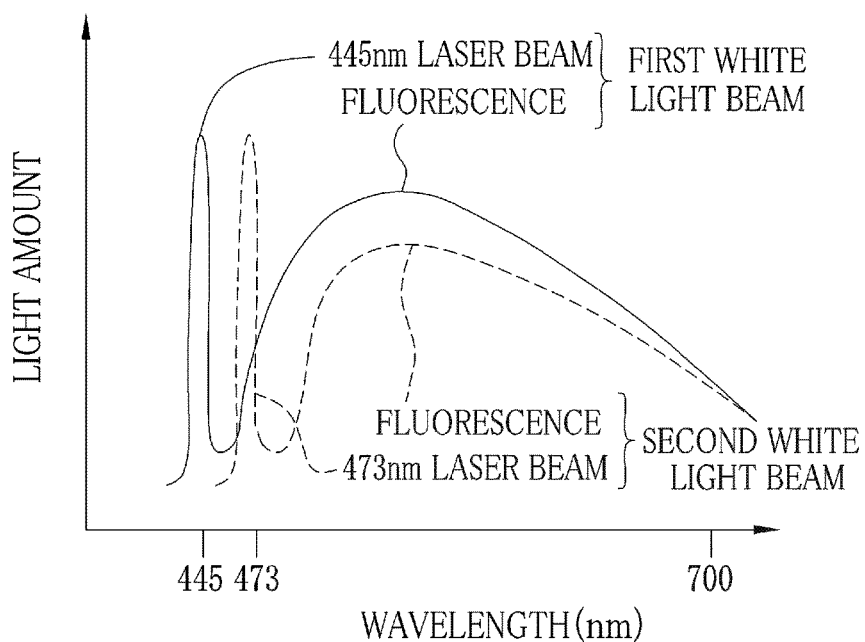
FIG. 3 is a graph showing emission spectra of first and second white light beams.

As shown in FIG. 3, the first white light beam has a wavelength of 445 nm being a wavelength band of the first laser beam and wavelengths between 460 nm and 700 nm being a wavelength band of the fluorescence produced by the entrance of the first laser beam. The second white light beam has a wavelength of 473 nm being a wavelength band of the second laser beam and wavelengths between 480 nm and 700 nm being a wavelength band of the fluorescence produced by the entrance of the second laser beam.

Note that, in the present invention, the white light beam does not necessarily contain each and every wavelength component of visible light, as long as it contains a plurality of wavelength components of R (red), G (green), and B (blue) being primary colors, such as the pseudo white light beam described above. In a broad sense, the white light beam includes, for example, light having wavelength components from green to red, light having wavelength components from blue to green, and the like.

An optical system such as an objective lens unit (not shown) for capturing image light of the internal body portion is provided in the recess of the imaging window 42. In the recess of the objective lens unit, an image sensor 60 e.g. a CCD image sensor or a CMOS image sensor is provided to perform photoelectric conversion of the image light.

The image sensor 60 receives the image light from the objective lens unit at its light receiving surface (imaging surface), and performs the photoelectric conversion of the received image light to output an analog image signal. The image sensor 60 is a color CCD. In the light receiving surface of the image sensor 60, pixel groups each including an R pixel having an R color filter, a G pixel having a G color filter, and a B pixel having a B color filter are arranged into a matrix.

Figure 4:
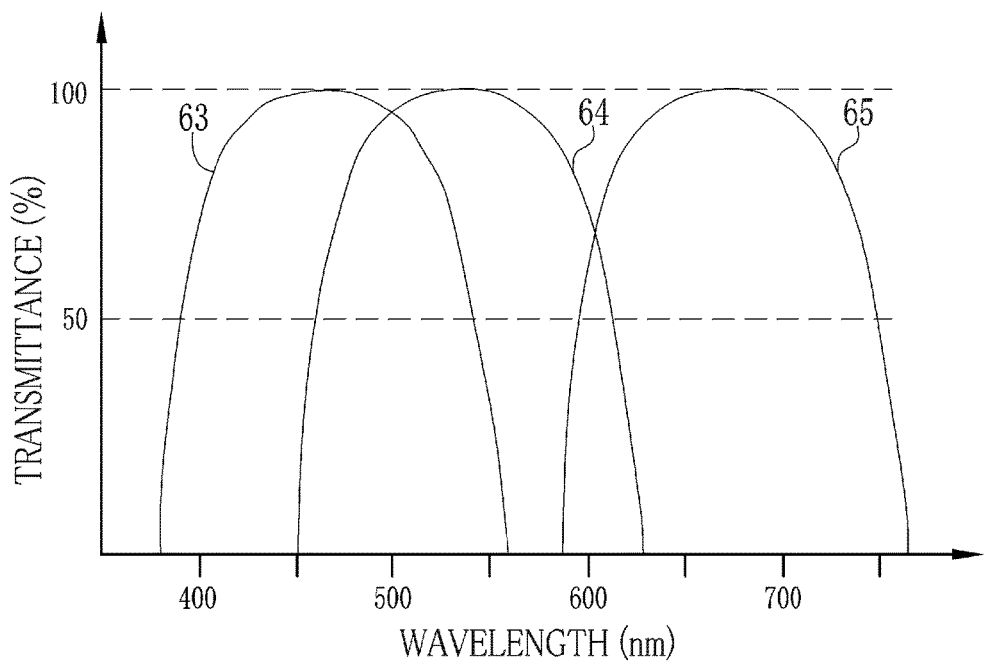
FIG. 4 is a graph showing spectral transmittance of R, G, and B color filters.

The B, G, and R color filters have spectral transmittance represented by curves 63, 64, and 65 of FIG. 4, respectively. Accordingly, the white light beam that is applied to the internal body portion and reflected therefrom is incident upon every pixel of the image sensor 60.

The image signal outputted from the image sensor 60 is inputted to an A/D converter 68 through a cable 67. The A/D converter 68 converts the image signal into a digital image signal. The converted image signal is inputted to an image processing unit 73 of the processor device 13 through the connector 36.

Figure 5A:
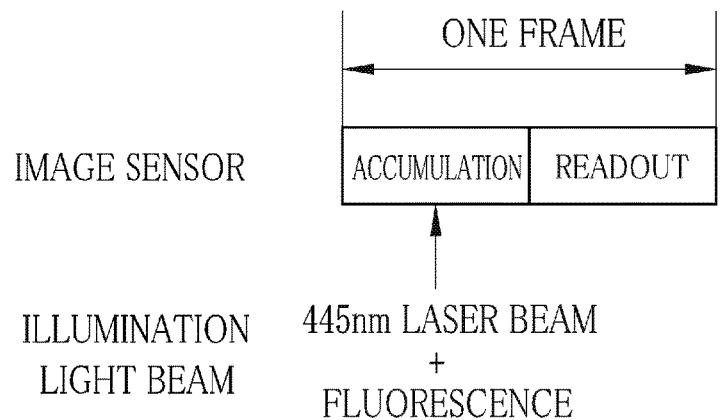
FIG. 5A is an explanatory view of imaging control of an image sensor in a normal mode.

An imaging controller 70 controls the image sensor 60. As shown in FIG. 5A, in the normal mode, accumulation and readout of electric charge that is produced by irradiation with the first white light beam (445 nm+fluorescence) are performed within one frame period. This accumulation and readout are repeated while the endoscope system 10 stays in the normal mode.

Figure 5B:
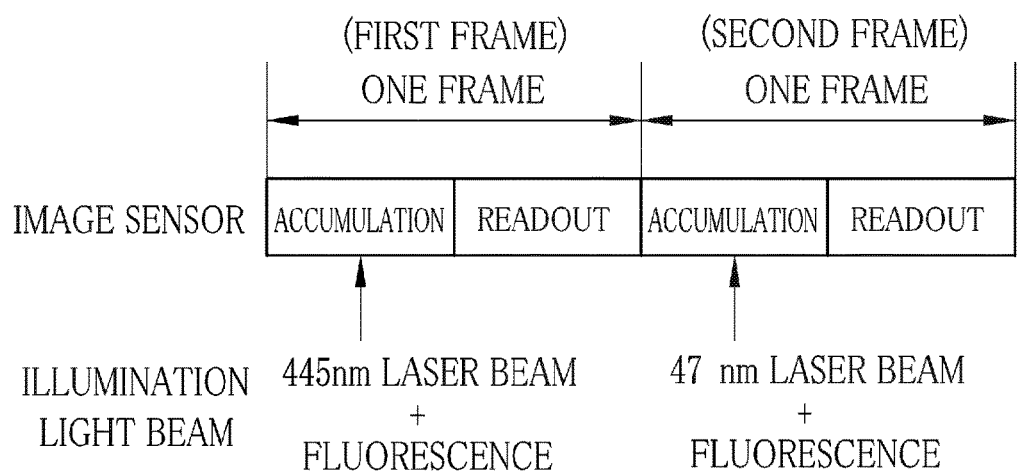
FIG. 5B is an explanatory view of imaging control of the image sensor in a special mode.

In the special mode, on the other hand, as shown in FIG. 5B, accumulation and readout of the electric charge that is produced by irradiation with the first white light beam are performed in a first frame. After that, accumulation and readout of electric charge that is produced by irradiation with the second white light beam (473 nm+fluorescence) are performed in a second frame. The first and second frames are alternately repeated while the endoscope system 10 stays in the special mode.

In the special mode, B1 represents a blue signal outputted from the B pixels of the image sensor 60 in the first frame. G1 represents a green signal outputted from the G pixels in the first frame, and R1 represents a red signal outputted from the R pixels outputted from the R pixels in the first frame. Similarly, B2 represents a blue signal outputted from the B pixels in the second frame. G2 represents a green signal outputted from the G pixels in the second frame, and R2 represents a red signal outputted from the R pixels in the second frame.

The processor device 13 is constituted of a main controller 72, the image processing unit 73, and storage 74. The main controller 72 is connected to the monitor 14 and the input device 15. The main controller 72 controls the image processing unit 73, the source controller 20 of the light source device 11, the imaging controller 70 of the electronic endoscope 12, and the monitor 14 based on input from the mode switch 17 of the electronic endoscope 12 and the input device 15.

The image processing unit 73, which includes a normal image processor 80 and a special image processor 82, applies predetermined image processing to the image signal from the electronic endoscope 12. The normal image processor 80 applies the predetermined image processing to the image signal obtained in the normal mode to produce a normal image.

The special image processor 82 calculates an oxygen saturation level of blood based on the image signals obtained in the special mode, and produces a special image (oxygen saturation image) in which the normal image is artificially colored in accordance with the oxygen saturation level. The special image processor 82 includes a displacement calculator 83, a signal ratio calculator 84, a correlation memory 85, an oxygen saturation level calculator 86, and a special image generator 88.

The displacement calculator 83 calculates a displacement $\Delta F$ between the image of the first frame and the image of the second frame. The displacement $\Delta F$ is calculated from the green signal G1 of the first frame and the green signal G2 of the second frame, because of similarity in signal characteristics therebetween. First, as shown in (A) of FIG. 6, in each of the green signals G1 and G2, square areas Ai ("i" represents natural numbers from 1 to n) each consisting of 3 by 3 pixels are set up. Note that, in the image signal e.g. the green signals G1 and G2, an X direction represents a vertical direction, and a Y direction represents a horizontal direction.

Figure 6:
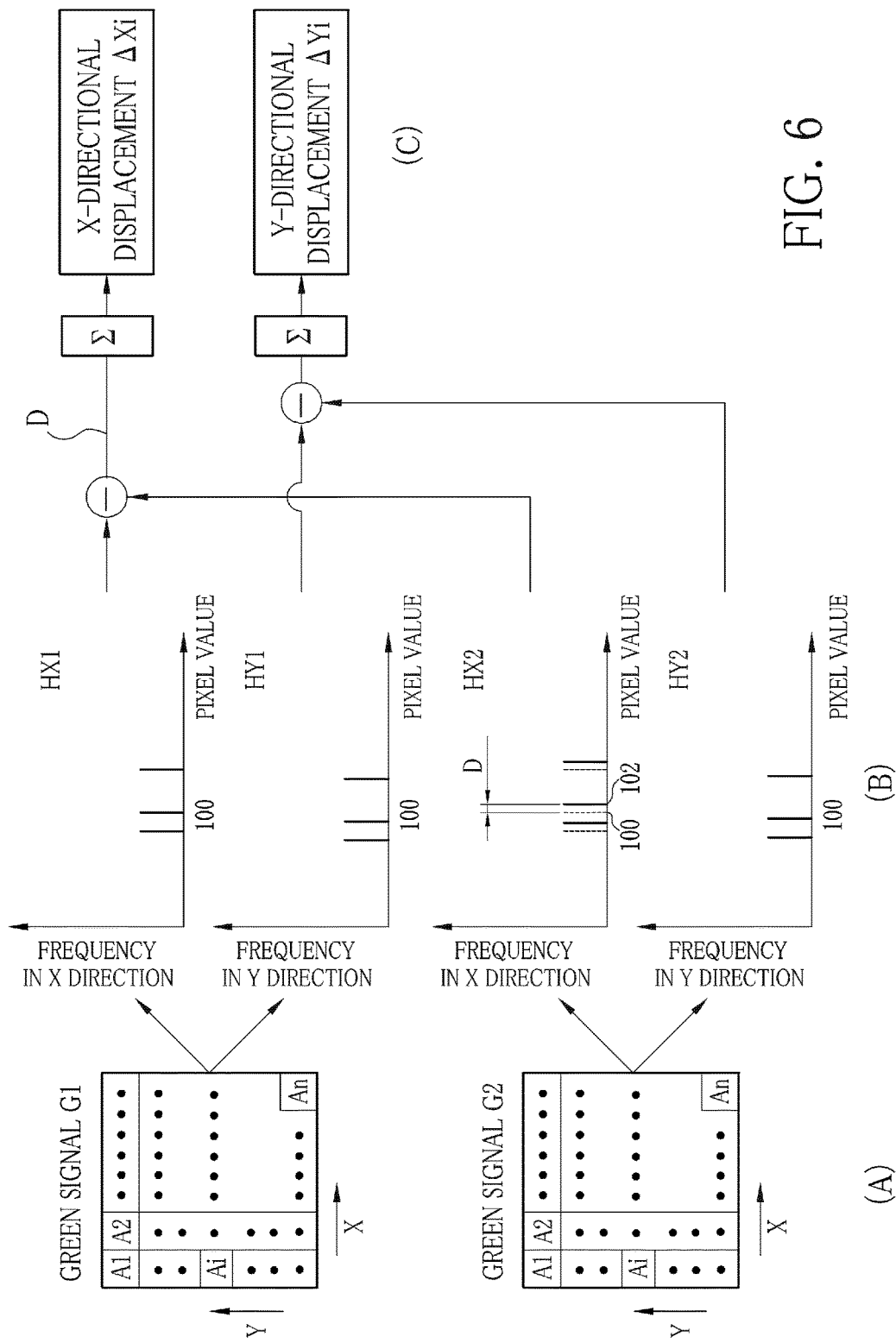
FIG. 6 is an explanatory view of a method for calculating displacement in X and Y directions in a square area Ai.

Next, as show in (B) of FIG. 6, in each square area Ai, a cumulative histogram HX1 in the X direction and a cumulative histogram HY1 in the Y direction are produced from the green signal G1. The cumulative histogram represents frequency (the number of occurrence) of each pixel value in the X or Y direction of the square area Ai. In the cumulative histogram, a vertical axis represents the frequency, and a horizontal axis represents the pixel value. In a like manner, a cumulative histogram HX2 in the X direction and a cumulative histogram HY2 in the Y direction are produced from the green signal G2.

After that, as shown in (C) of FIG. 6, an X-directional displacement ΔXi is calculated by comparison between the cumulative histograms HX1 and HX2. In a like manner, a Y-directional displacement ΔYi is calculated by comparison between the cumulative histograms HY1 and HY2. The comparison operation is preferably subtraction operation between the cumulative histograms HX1 and HX2 or between the cumulative histograms HY1 and HY2. Taking the cumulative histograms HX1 and HX2 as an example, the frequency at a pixel value 100 in the cumulative histogram HX1 corresponds to the frequency at a pixel value 102 in the cumulative histogram HX2. Thus, subtraction between the pixel values 102 and 100 results in a difference value D (2 pixel values). The difference value D is calculated with respect to every pixel value in the cumulative histograms, and the sum total of the calculated difference values D is referred to as the X-directional displacement ΔXi. The Y-directional displacement ΔYi is calculated in a like manner.

Figure 7:
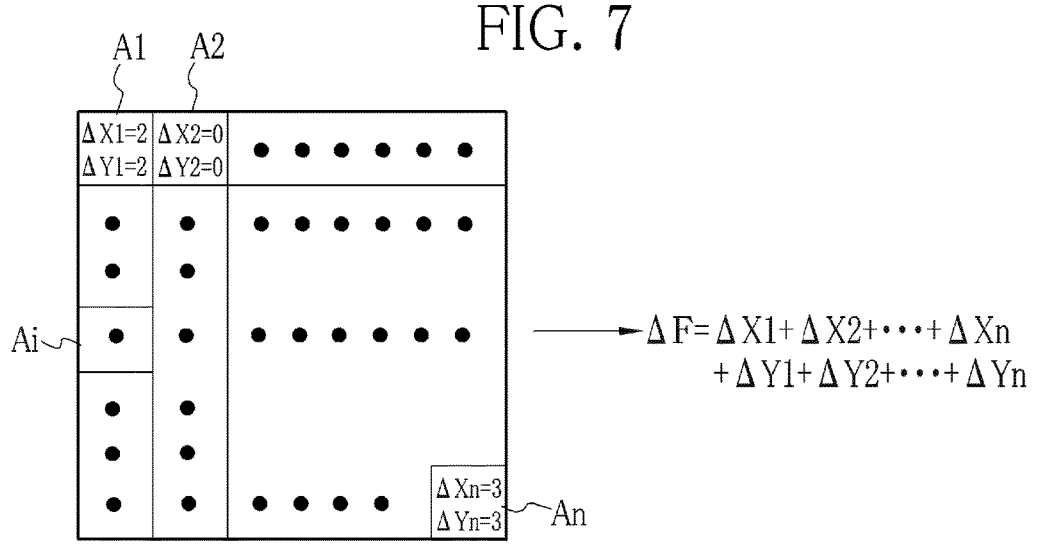
FIG. 7 is an explanatory view of a method for calculating positional displacement between frames.

After the X- and Y-directional displacements ΔXi and ΔYi are calculated from the green signals G1 and G2, as shown in FIG. 7, the X- and Y-directional displacements ΔXi and ΔYi of every square area Ai are totalized to obtain the displacement ΔF between the first and second frames. Note that, one of the X- and Y-directional displacements ΔXi and ΔYi may be used to calculate the displacement ΔF.

The signal ratio calculator 84 calculates a signal ratio B2/G1 between the blue signal B2 of the second frame and the green signal G1 of the first frame, and a signal ratio R1/G1 between the red signal R1 of the first frame and the green signal G1 of the first frame. The signal ratio calculator 84 calculates the signal ratios with respect to the pixel situated in the same position. The signal ratios are calculated with respect to each and every pixel. Note that, the signal ratios may be calculated only in pixels composing a blood vessel area out of all pixels of the image signal. In this case, the blood vessel area is determined based on difference in the image signal between the blood vessel area and the other area.

Figure 8:
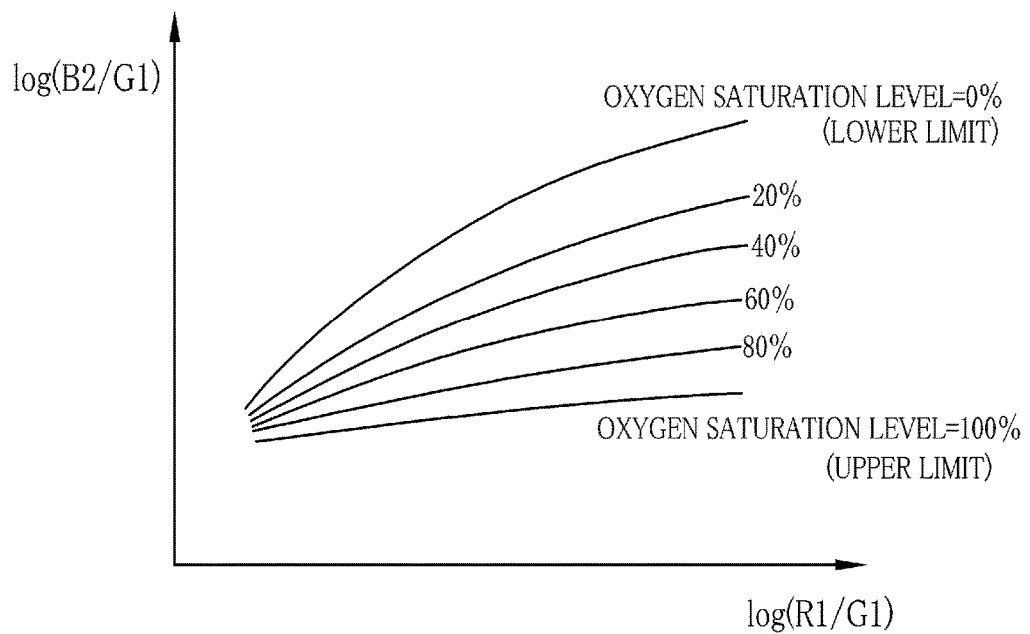
FIG. 8 is a graph showing the correlation among an oxygen saturation level and signal ratios.

The correlation memory 85 stores the correlation among the signal ratios B2/G1 and R1/G1 and the oxygen saturation level. As shown in FIG. 8, this correlation takes the form of a two-dimensional table in which contour lines representing the oxygen saturation level are defined in two-dimensional space. The position and shape of the contour lines are obtained by physical simulation of light scattering, and are variable in accordance with blood volume. For example, variation in the blood volume widens or narrows distance between the contour lines. Note that, the signal ratios B2/G1 and R1/G1 are depicted in log scale.

Figure 9:
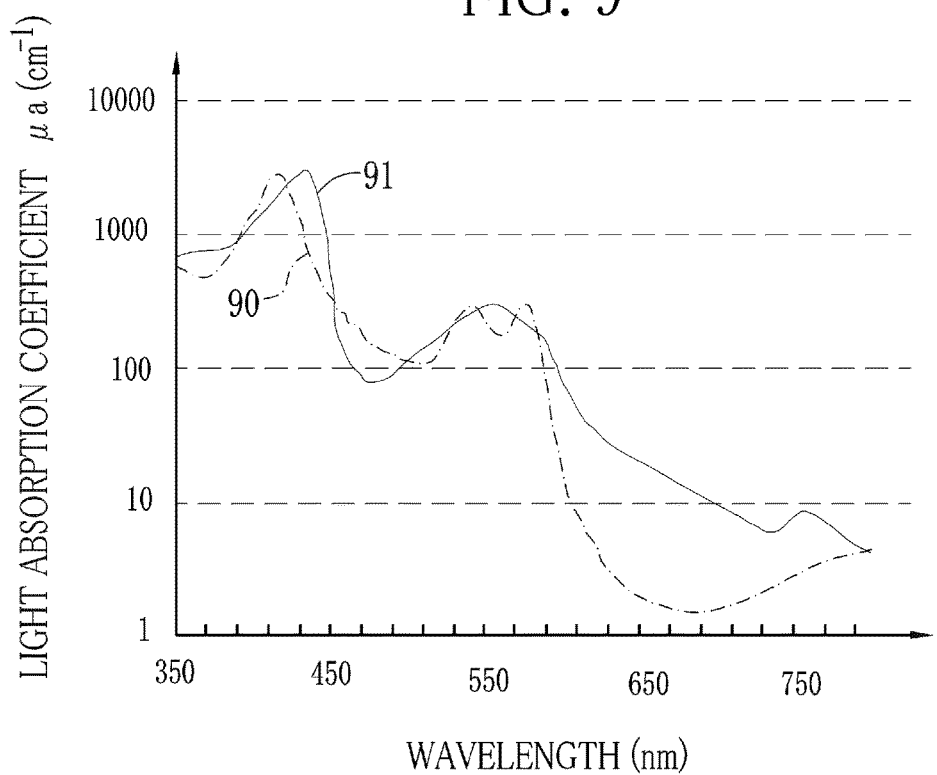
FIG. 9 is a graph showing a light absorption coefficient of oxygenated hemoglobin and deoxygenated hemoglobin.

The correlation is closely related to the light absorbing property and light scattering property of oxygenated hemoglobin and deoxygenated hemoglobin, as shown in FIG. 9. In FIG. 9, a line 90 represents a light absorption coefficient of the oxygenated hemoglobin, and a line 91 represents a light absorption coefficient of the deoxygenated hemoglobin. The use of a wavelength of, for example, 473 nm at which the light absorption coefficient much differs between the oxygenated hemoglobin and the deoxygenated hemoglobin allows the obtainment of the oxygen saturation level.

However, the blue signal B2 that contains a signal corresponding to a light beam of 473 nm is highly dependent not only on the oxygen saturation level but also on the blood volume. Therefore, the use of the signal ratios B2/G1 and R1/G1, which are obtained from the red signal R1 that is mainly dependent on the blood volume and the green signal G1 being a reference signal (standardization signal) of the blue signal B2 and the red signal R1, in addition to the blue signal B2, allows the obtainment of the oxygen saturation level with high accuracy while eliminating the influence of the blood volume. To calculate the oxygen saturation level without being influenced by the blood volume, the blue signal B2 and the red signal R1 preferably have wavelengths within a range of 460 to 700 nm.

The following three items hold true according to the dependence of the light absorption coefficient on a wavelength:

(1) In the vicinity of a wavelength of 470 nm (for example, a blue wavelength range having a center wavelength of 470 nm±10 nm), the light absorption coefficient largely varies in accordance with difference in the oxygen saturation level.

(2) In a green wavelength range between 540 and 580 nm, a mean value of the light absorption coefficient is insusceptible to the oxygen saturation level.

(3) In a red wavelength range between 590 and 700 nm, the light absorption coefficient seems to vary largely in accordance with the oxygen saturation level, but in actual fact, is insusceptible to the oxygen saturation level because a value of the light absorption coefficient is very small.

Figure 10:
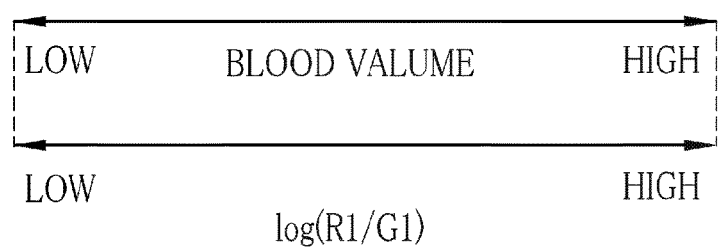
FIG. 10 is a graph showing the correlation between blood volume and the signal ratio.

The correlation memory 85 also stores the correlation between the signal ratio R1/G1 and the blood volume as shown in FIG. 10. This correlation takes the form of a one-dimensional table in which the blood volume is increased with increase in the signal ratio R1/G1. The correlation between the signal ratio R1/G1 and the blood volume is used in calculation of the blood volume.

Figure 11:
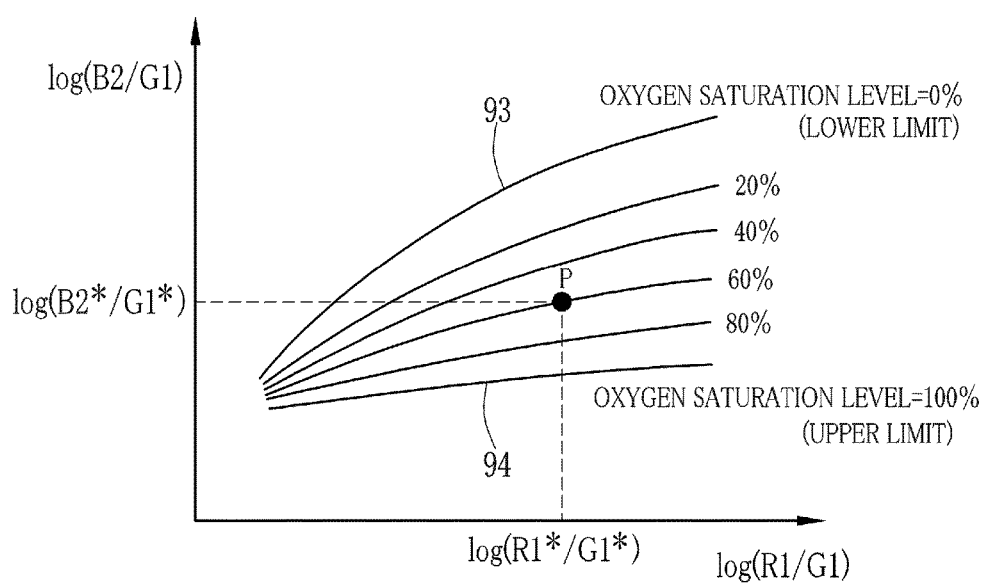
FIG. 11 is an explanatory view of a method for calculating the oxygen saturation level from the signal ratios in FIG. 8.

The oxygen saturation level calculator 86 calculates the oxygen saturation level of each pixel with the use of the correlations stored in the correlation memory 85 and the signal ratios B2/G1 and R1/G1 obtained by the signal ratio calculator 84. As shown in FIG. 11, a point P that corresponds to the signal ratios B2*/G1* and R1*/G1* obtained by the signal ratio calculator 84 is determined in the correlation stored in the correlation memory 85. If the point P is situated between a lower limit line 93 representing an oxygen saturation level of 0% and an upper limit line 94 representing an oxygen saturation level of 100%, the point P indicates the percentile of the oxygen saturation level. Taking FIG. 11 as an example, the point P is situated in the contour line of 60%, so the oxygen saturation level is 60%.

On the other hand, in a case where the point is out of the range between the lower limit line 93 and the upper limit line 94, if the point is situated above the lower limit line 93, the oxygen saturation level is determined to be 0%. If the point is situated below the upper limit line 94, the oxygen saturation level is determined to be 100%. Note that, in a case where the point is out of the range between the lower limit line 93 and the upper limit line 94, it may be judged that the oxygen saturation level of that pixel has low reliability and should not be displayed on the monitor 14.

The special image generator 88 produces the special image based on the displacement ΔF obtained by the displacement calculator 83 and the oxygen saturation level obtained by the oxygen saturation level calculator 86. The produced special image is displayed on the monitor 14. This special image is represented by a video signal composed of a luminance signal Y and color difference signals Cb and Cr.

The green signal G1 of the first frame is assigned as the luminance signal Y. As the color difference signals Cb and Cr, a signal value corresponding to the oxygen saturation level is assigned based on any of first to third color tables $88a$ to $88c$.

Figure 12A:
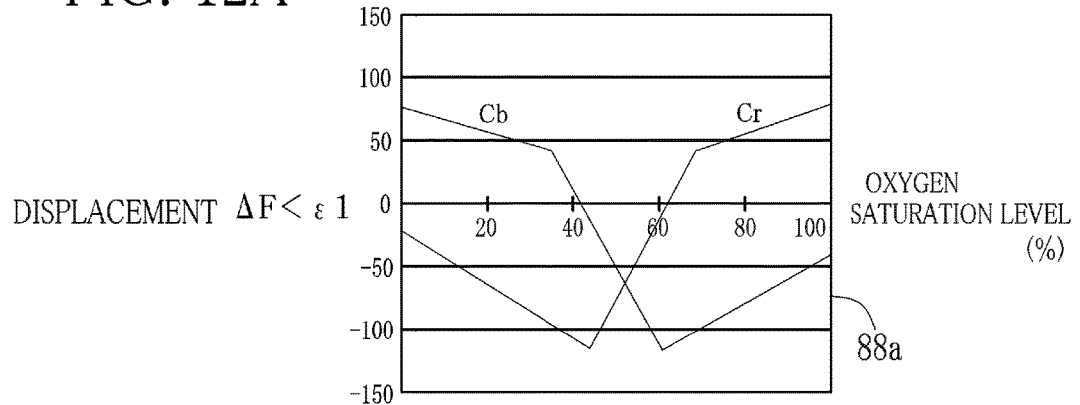
FIG. 12A is a graph showing a first color table that is used in a case where the displacement is less than a first allowable value.
Figure 12B:
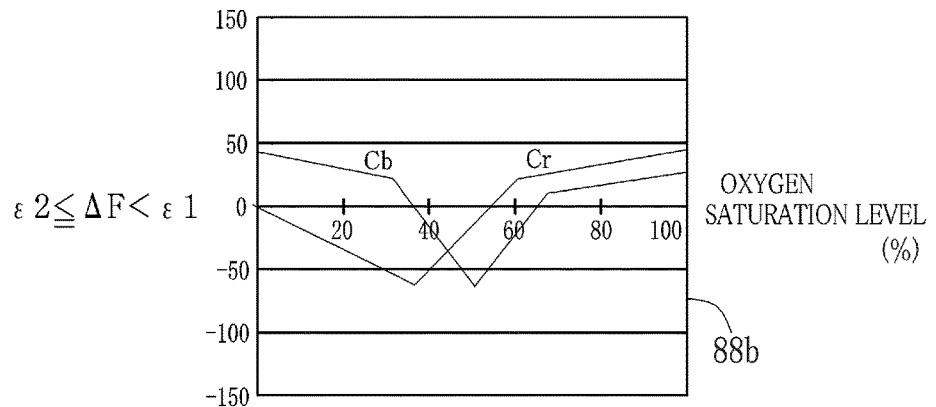
FIG. 12 B is a graph showing a second color table that is used in a case where the displacement is the first allowable value or more and less than a second allowable value.
FIG. 12C is a graph showing a third color table that is used in a case where the displacement is the second allowable value or more.
Figure 12C:
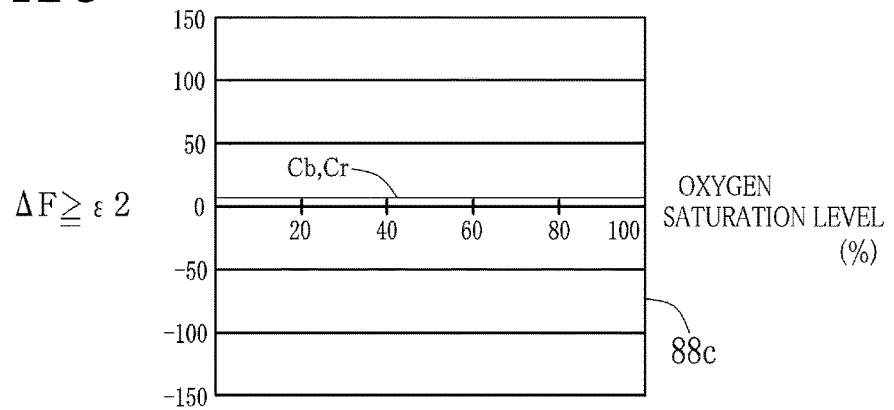

The first color table $88a$ shown in FIG. 12A is used if the displacement $\Delta F$ is less than a first allowable value $\varepsilon 1$. The second color table $88b$ shown in FIG. 12B is used if the displacement $\Delta F$ is the first allowable value $\varepsilon 1$ or more and less than a second allowable value $\varepsilon 2$ ($\varepsilon 2 > \varepsilon 1$). The third color table $88c$ shown in FIG. 12C is used if the displacement $\Delta F$ is the second allowable value $\varepsilon 2$ or more. In the second color table $88b$, a chroma of an artificial color is set lower than that in the first color table $88a$. The first and second color tables $88a$ and $88b$ artificially color the oxygen saturation level with chromatic color, while the third table $88c$ artificially colors the oxygen saturation level with achromatic color. Note that, any color property other than the chroma of the artificial color may be different among the color tables in accordance with the displacement $\Delta F$.

As described above, since the used color table is changed depending on the displacement $\Delta F$, in other words, the larger the displacement $\Delta F$, the lower the chroma of the artificial color becomes, it is possible to notify a user of the reliability of the oxygen saturation level at sight by change of color. In a case where the displacement $\Delta F$ is so large as to exceed the second allowable value $\varepsilon 2$ (the head assembly 40 is moved extremely fast), the third color table for the achromatic color, which converts the special image into a gray scale image, is used. Therefore, the user is notified at the sight of the monitor 14 that the obtained gray scale special image is clearly different from the colored special image with high reliability.

Next, the operation of the present invention will be described with referring to a flowchart of FIG. 13. In the normal mode, the inert unit 32 of the electronic endoscope 12 is inserted into the patient's body cavity. The insertion state is displayed on the monitor 14. The head assembly 40 is aimed at a desired portion inside the body for observation. When a body portion suspected to be a lesion is found out, the endoscope system 10 is put into the special mode by operation of the mode switch 17. The first laser beam having a center wavelength of 445 nm is emitted from the first laser source LD1. The first laser beam excites the phosphor 50. The first white light beam from the phosphor 50 is applied to the body portion. The reflected light beam from the body portion is captured by the image sensor 60 being the color CCD having the B, G, and R pixels. The image sensor 60 produces the image signal of the first frame that includes the blue signal B1, the green signal G1, and the red signal R1.

Then, the second laser beam having a center wavelength of 473 nm excites the phosphor 50, and the obtained second white light beam is applied to the body portion. The image sensor 60 captures the reflected light beam from the body portion, and produces the image signal of the second frame that includes the blue signal B2, the green signal G2, and the red signal R2.

The displacement calculator 83 calculates the displacement $\Delta F$ between the first and second frames from the green signal G1 of the first frame and the green signal G2 of the second frame. The signal ratio calculator 84 calculates the signal ratios B2/G1 and R1/G1 with respect to the pixel situated in the same position in the image signals between the first and second frames. The signal ratios of every pixel are calculated. After that, the oxygen saturation level calculator 86 calculates the oxygen saturation level corresponding to the signal ratios B2/G1 and R1/G1 based on the correlations stored in the correlation memory 85. The oxygen saturation level is obtained for each and every pixel.

After the obtainment of the oxygen saturation level and blood volume of every pixel, the special image generator 88 obtains the color difference signals Cr and Cb corresponding to the oxygen saturation level with the use of one of the first to third color tables $88a$ to $88c$ chosen in accordance with the displacement $\Delta F$. The green signal G1 of the first frame is assigned as the luminance signal Y. The color difference signals Cr and Cb and the luminance signal Y compose the special image. The produced special image is displayed on the monitor 14. In the special image, a hue indicates the oxygen saturation level, and the chroma indicates the reliability of the oxygen saturation level.

Figure 14:
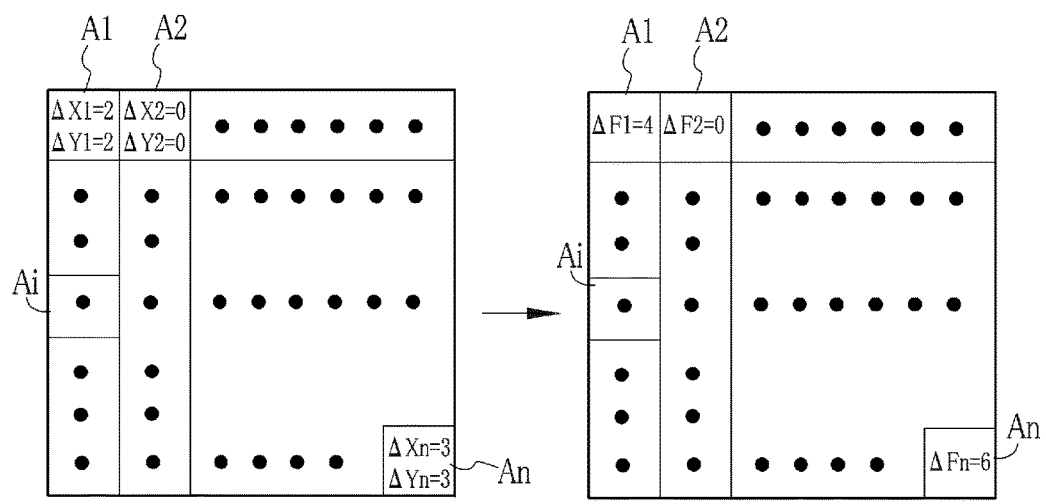
FIG. 14 is an explanatory view of a method for calculating the displacement in each square area.
Figure 15:
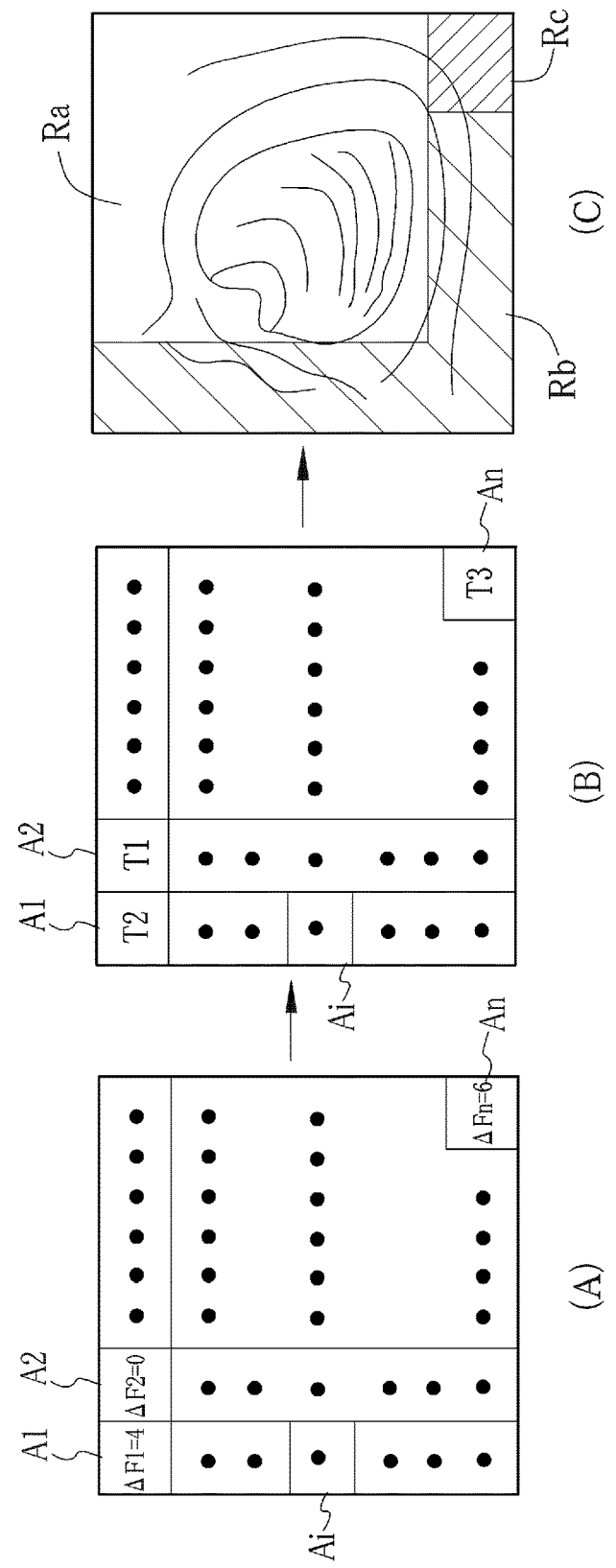
FIG. 15 is an explanatory view of a method for producing a special image that is colored differently from region to region depending on an amount of displacement.

FIGS. 14 and 15 show a second embodiment of the present invention. In the second embodiment, the chroma of the artificial color is changed on a square area Ai basis based on the X- and Y-directional displacements $\Delta Xi$ and $\Delta Yi$ of each square area Ai, while in the first embodiment the chroma of the artificial color is changed on an entire image basis based on the displacement $\Delta F$ of the entire image. The structure of the second embodiment is the same as that of the first embodiment except for the displacement calculator 83 and the special image generator 88, the description of the same components will be omitted. Note that, the square area Ai is preferably defined to have three pixels in the X direction and three pixels in the Y direction, as with the first embodiment, but is not limited to this configuration.

As with the first embodiment, the displacement calculator 83 of the second embodiment calculates the X- and Y-directional displacements $\Delta Xi$ and $\Delta Yi$ of each square area Ai with the use of the cumulative histograms HX1 and HX2 in the X direction and the cumulative histograms HY1 and HY2 in the Y direction (see FIG. 6). After that, as shown in FIG. 14, the X- and Y-directional displacements $\Delta Xi$ and $\Delta Yi$ are added on a square area Ai basis to obtain a displacement $\Delta Fi$ of each square area Ai.

The special image generator 88 of the second embodiment assigns the green signal G1 of the first frame as the luminance signal Y, as with the first embodiment. As for the color difference signals Cr and Cb, on the other hand, the special image generator 88 calculates signal values based on one of the first to third color tables $88a$ to $88c$ assigned on a square area Ai basis. If the displacement $\Delta Fi$ of the square area Ai is less than the first allowable value $\varepsilon 1$, the first color table $88a$ is used. If the displacement $\Delta Fi$ is the first allowable value $\varepsilon 1$ or more and less than the second allowable value $\varepsilon 2$ ($\varepsilon 2 > \varepsilon 1$), the second color table $88b$ is used. If the displacement $\Delta Fi$ is the second allowable value $\varepsilon 2$ or more, the third color table $88c$ is used.

Thus, in the case of FIG. 15, (A) shows the displacement $\Delta Fi$ of each square area Ai. As shown in (B), one of the first to third color tables $88a$ to $88c$ is assigned to each square area Ai depending on its displacement $\Delta Fi$. In (B), "T1" represents the first color table $88a$, and "T2" represents the second color table $88b$, and "T3" represents the third color table $88c$. Based on one of the first to third color tables $88a$ to $88c$ assigned to each square area Ai, the color difference signals Cr and Cb are obtained on a square area Ai basis. The obtained color difference signals Cr and Cb and the luminance signal Y compose the special image.

In the special image, as shown in (C), a region Ra enclosing the square areas Ai that use the first color table $88a$ (T1) is displayed in the chromatic color with high chroma, so the user is notified at sight that the region Ra has high reliability of the oxygen saturation level. A region Rb enclosing the square areas Ai that use the second color table 88b (T2) is displayed in the chromatic color but has low chroma, so the user is notified at sight that the region Rb has relatively low reliability of the oxygen saturation level. A region Rc enclosing the square areas Ai that use the third color table 88c (T3) is displayed in the achromatic color, so the use is notified at sight that the region Rc has extremely low reliability of the oxygen saturation level. Accordingly, since the region (Ra) having the high chroma and the regions (Rb and Rc) having the low chroma are mixed in the special image, the user can recognize all the regions at the same time.

Figure 16:
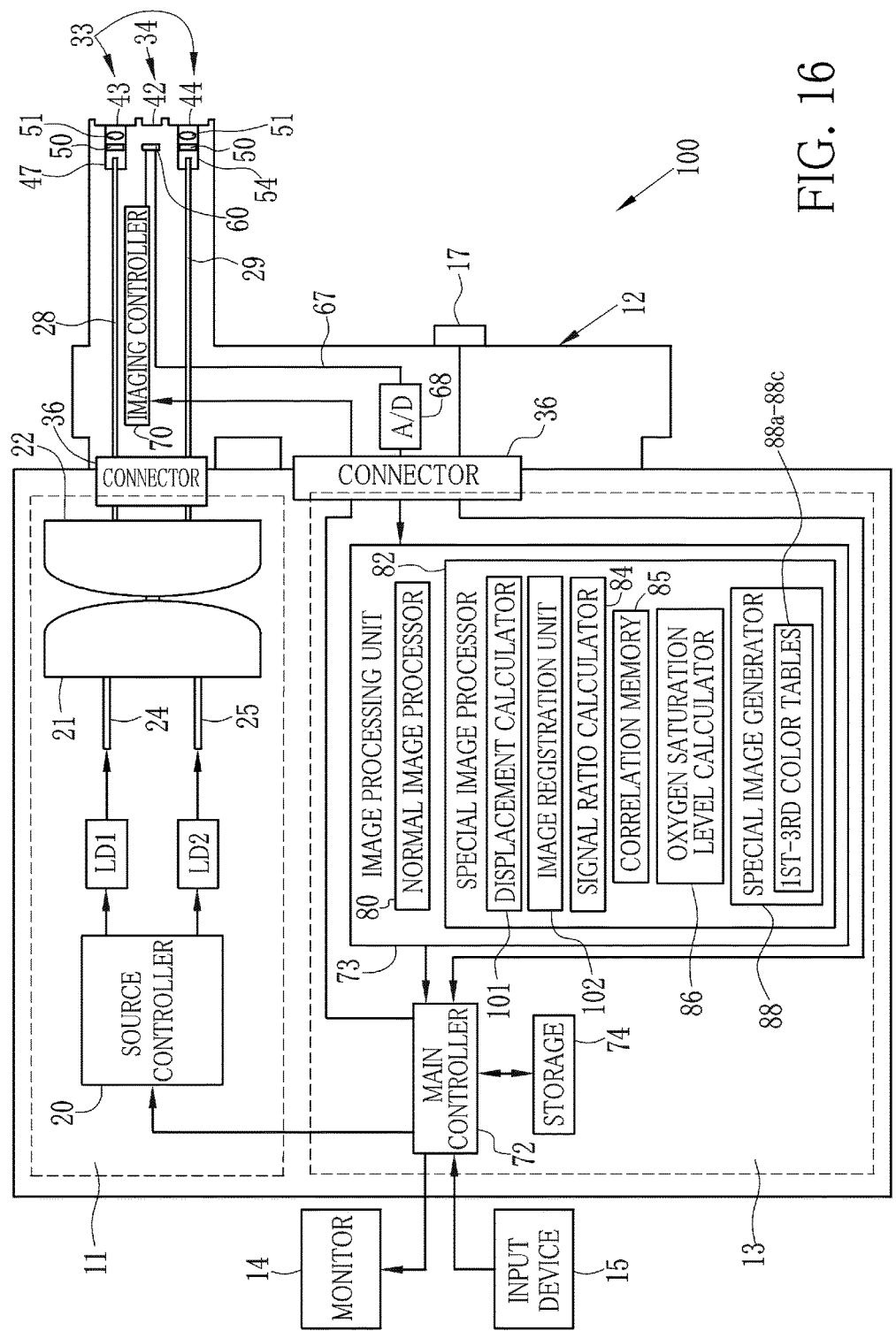
FIG. 16 is a block diagram of an endoscope system according to a third embodiment.

In a third embodiment shown in FIG. 16, after image registration is performed based on a displacement between the first and second frames, the displacement between the first and second frames is calculated again. An endoscope system 100 according to the third embodiment is provided with a displacement calculator 101 for calculating displacements ΔFx and ΔFy used in the image registration, and an image registration unit 102 for performing the image registration between the first and second frames based on the displacements ΔFx and ΔFy. The special image generator 88 of the third embodiment produces the special image in a way different from that of the first embodiment. The other structure and components are the same as those of the first embodiment, so the description thereof will be omitted.

Figure 17:
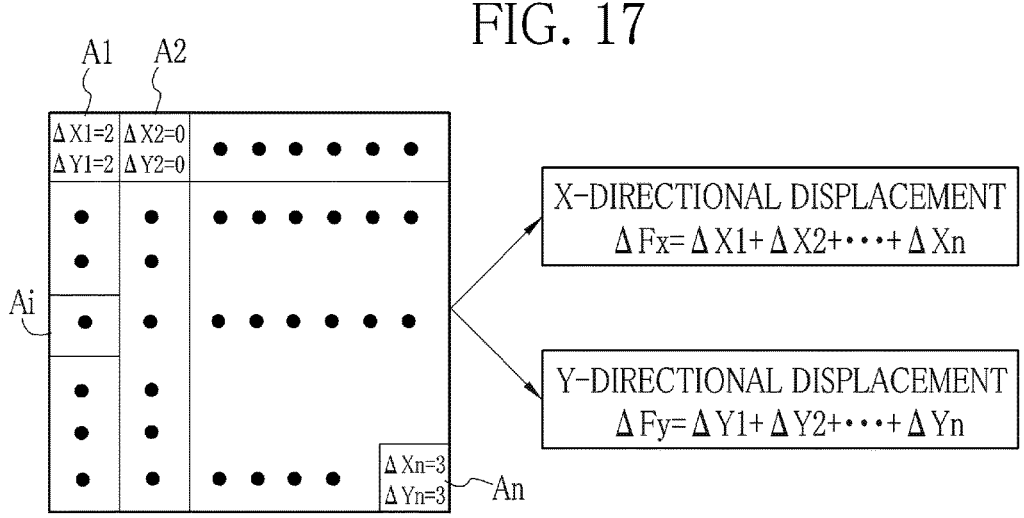
FIG. 17 is an explanatory view of a method for calculating displacement of the entire image from the X- and Y-directional displacement of each square area.

As with the displacement calculator 83 of the first embodiment, the displacement calculator 101 calculates the X- and Y-directional displacements ΔXi and ΔYi of each square area Ai with the use of the cumulative histograms HX1 and HX2 in the X direction and the cumulative histograms HY1 and HY2 in the Y direction. After that, as shown in FIG. 17, all the X-directional displacements ΔXi (i=1 to n) are added to obtain an X-directional displacement ΔFx of the entire image signal. All the Y-directional displacements ΔYi (i=1 to n) are added to obtain a Y-directional displacement ΔFy of the entire image signal.

Figure 18A:
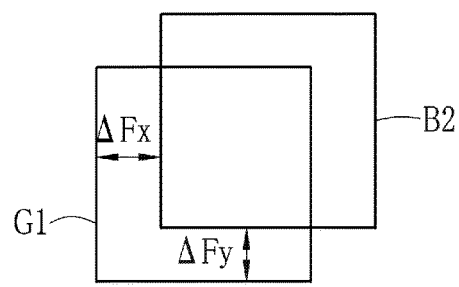
FIG. 18A is an explanatory view for explaining image registration between a blue signal and a green signal.
Figure 18B:
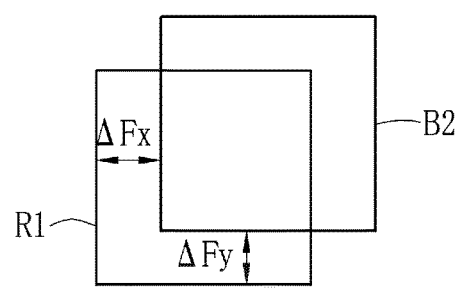
FIG. 18B is an explanatory view for explaining image registration between the blue signal and a red signal.

The image registration unit 102 performs the image registration among the signals used for calculation of the oxygen saturation level, and more specifically, between the green signal G1 of the first frame and the blue signal B2 of the second frame, and between the red signal R1 of the first frame and the blue signal B2 of the second frame. First, as shown in FIG. 18A, one of the green signal G1 and the blue signal B2 is shifted by the X-directional displacement ΔFx in the X direction, and by the Y-directional displacement ΔFy in the Y direction. In a like manner, as shown in FIG. 18B, one of the red signal R1 and the blue signal B2 is shifted by the X-directional displacement ΔFx in the X direction, and by the Y-directional displacement ΔFy in the Y direction.

After the image registration unit 102 performs the image registration, the displacement calculator 101 calculates X- and Y-directional displacements again. Here, ΔFx' refers to a re-calculated X-directional displacement, and ΔFy' refers to a re-calculated Y-directional displacement. The special image generator 88 chooses one of the color tables 88a to 88c in accordance with a re-calculated displacement ΔF' that is the sum of the re-calculated X- and Y-directional displacements ΔFx' and ΔFy'. How to choose the color table is the same as that of the first embodiment, except for replacing the displacement ΔF with the re-calculated displacement ΔF'. With the use of the chosen color table, the special image is produced.

In the third embodiment, since the image registration unit 102 performs the image registration between the first and second frames, the reliability of the oxygen saturation level is improved in the special image. Even if the image regis-tration unit 102 cannot completely eliminate the displacement, the re-calculated displacements ΔFx' and ΔFy' after the image registration are indicated in the special image by change of color, so the user can recognize the displacement at the sight of the special image.

Note that, out of the three image signals of the R, G, and B wavelength bands used for calculation of the oxygen saturation level, one or two of the image signals may be produced using a semiconductor laser source as with the first embodiment, while the other image signals may be produced using a light beam separated from a broad-band light beam emitted from a white light source such as a xenon lamp.

Figure 19:
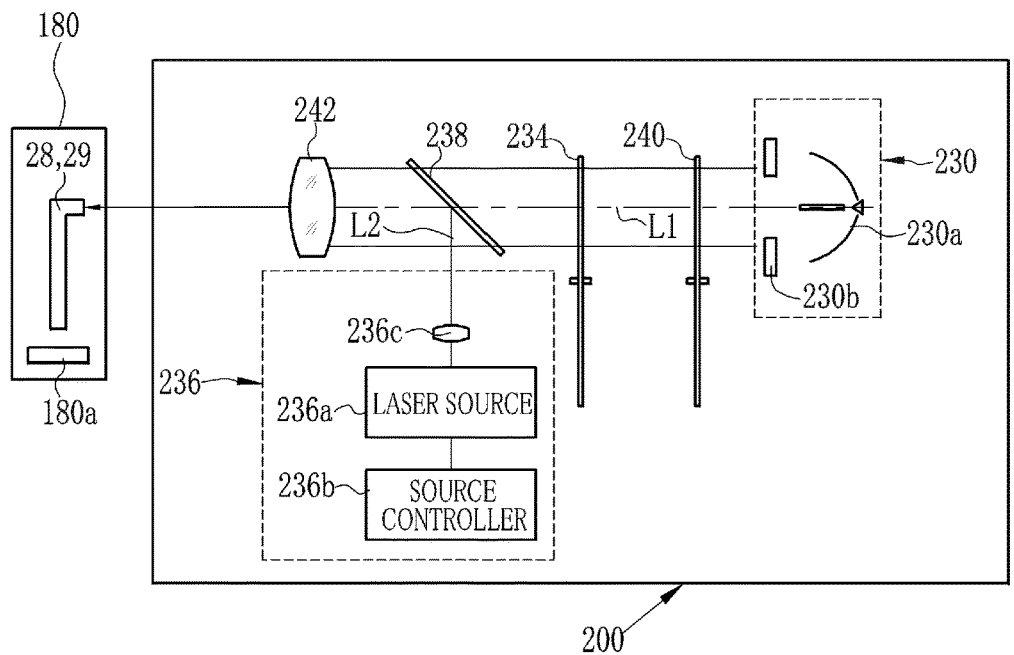
FIG. 19 is a schematic view of a light source device of the third embodiment.

In this case, a light source device 200 shown in FIG. 19 is used instead of the light source device 11 of the endoscope system 10 of the first embodiment. A light beam produced by the light source device 200 is supplied to an electronic endoscope 180. The electronic endoscope 180 has structure similar to that of the electronic endoscope 12 of the first embodiment, except that no phosphor 50 is provided in the lighting section 33 of the head assembly 40. Therefore, the light beam from the light source device 200 is directly applied to the internal body portion through the electronic endoscope 180.

An image sensor 180a provided in the electronic endoscope 180 has different structure from that of the image sensor 60. The operation of the imaging controller 70 is different from that of the first embodiment. In the processor device 13, the normal image processor 80 produces the normal image in a different way, and the special image processor 82 uses a signal different from that used in the first embodiment. Only the difference from the first embodiment will be described.

The light source device 200 is constituted of a white light source 230, a rotary filter 234, a semiconductor laser unit 236, a beam merger 238, and a shutter 240. The white light source 230 emits a broad-band light beam BB having wavelengths of 400 to 700 nm. The rotary filter 234 produces three color light beams of B, G, and R from the broad-band light beam BB emitted from the white light source 230, and sequentially supplies the three color light beams to the light guides 28 and 29. The semiconductor laser unit 236 emits a blue laser beam BN. The beam merger 238 merges an optical path L2 of the blue laser beam BN into an optical path L1 of the broad-band light beam BB. The shutter 240 closes the optical path L1 of the broad-band light beam BB between the white light source 230 and the rotary filter 234.

The white light source 230 includes a main body 230a for radiating the broad-band light beam BB and an aperture 230b for regulating the amount of the broad-band light beam BB. The main body 230a is a xenon lamp, a halogen lamp, a metal halide lamp, or the like. The opening of the aperture 230b is controlled by a light amount controller (not shown).

Figure 20:
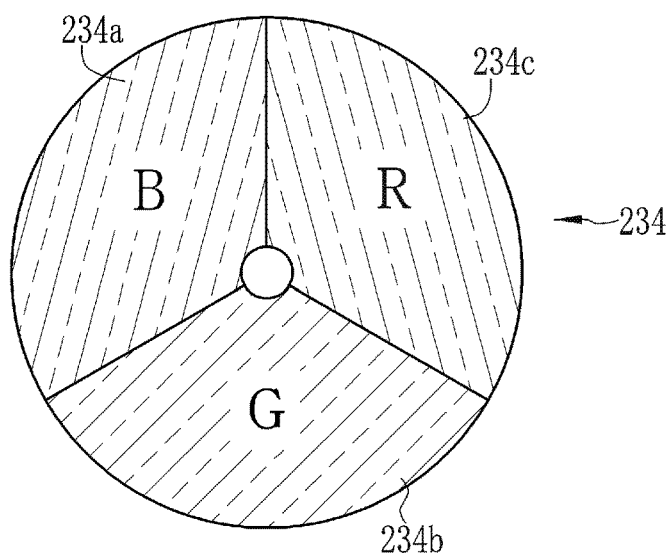
FIG. 20 is a plane view of a rotary filter.

As shown in FIG. 20, the rotary filter 234 is disposed rotatably so that a B filter 234a, a G filter 234b, and an R filter 234c are selectively inserted in the optical path L1 of the broad-band light beam BB. The rotary filter 234 is in a disc shape. The rotary filter 234 is divided into three sectors each having a central angle of 120° in its circumferential direction, and the B filter 234a, the G filter 234b, and the R filter 234c are disposed in the sectors.

Figure 21:
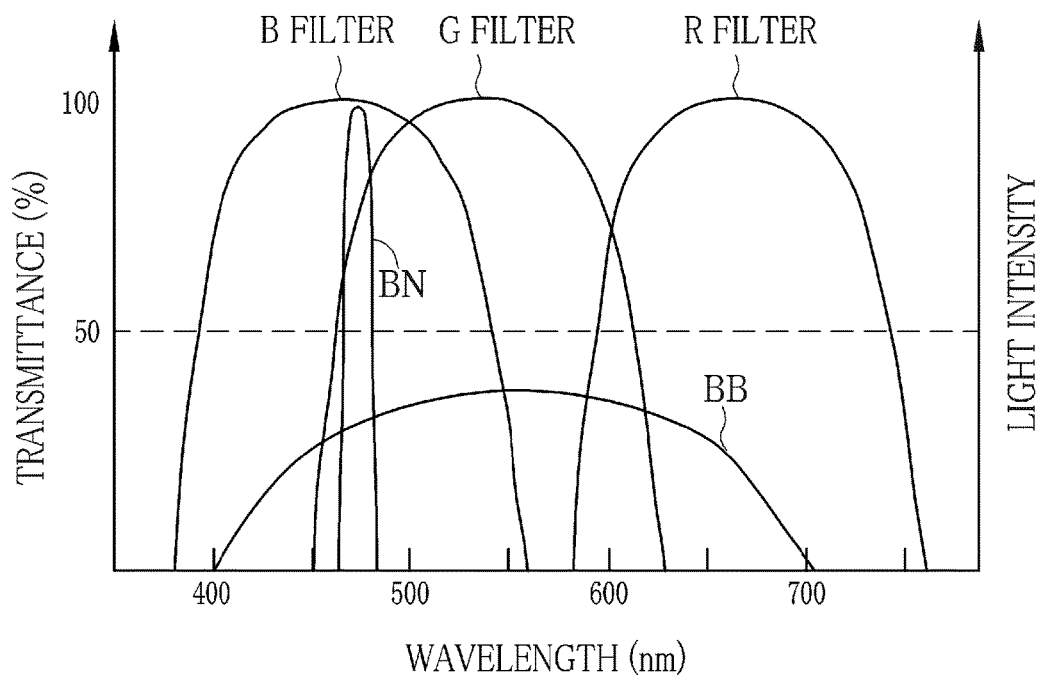
FIG. 21 is a graph showing the spectral transmittance of each of B, G, and R filters of the rotary filter and the emission spectra of a blue laser beam and a broad-band light beam.

As shown in FIG. 21, the B filter 234a transmits B light in a blue wavelength band out of the broad-band light beam BB. The G filter 234b transmits G light in a green wavelength band out of the broad-band light beam BB, and the R filter 234c transmits R light in a red wavelength band out of the broad-band light beam BB. Thus, by a turn of the rotary filter 234, B, G, and R light beams are sequentially emitted from the rotary filter 234.

The semiconductor laser unit 236 has the laser source 236*a* and the source controller 236*b*. As shown in FIG. 21, the laser source 236*a* emits the blue laser beam BN having a center wavelength of 473 nm. The source controller 236*b* controls the turn-on and -off of the laser source 236*a*. The source controller 236*b* is controlled by the main controller 72 of the processor device 13. The blue laser beam BN from the laser source 236*a* propagates through a condenser lens 236*c* to the beam merger 238.

The beam merger 238 being a dichroic mirror transmits the light from the rotary filter 234, while reflects the blue laser beam BN from the semiconductor laser unit 236 so as to merge the optical path L2 of the blue laser beam BN into the optical path L1 of the broad-band light beam BB. The light beam from the beam merger 238 is supplied to the electronic endoscope 180 through a condense lens 242.

Figure 22:
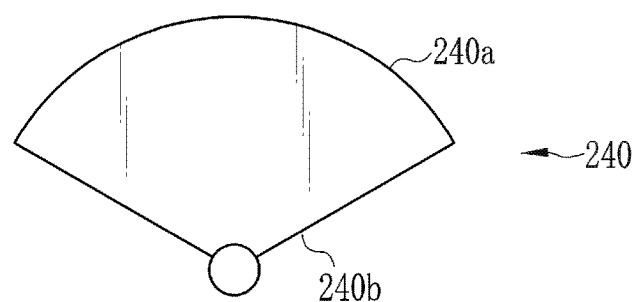
FIG. 22 is a plane view of a shutter.

As shown in FIG. 22, the shutter 240 has a light shielding portion 240*a* having a central angle of 120° for shielding the broad-band light beam BB, and a light transmitting portion 240*b* having a central angle of 240° for transmitting the broad-band light beam BB. The shutter 240 is made rotatable. By a turn of the shutter 240, the light shielding portion 240*a* and the light transmitting portion 240*b* are selectively and alternately inserted into the optical path L1 of the broad-band light beam BB.

The turning operation of the shutter 240 differs between the normal mode and the special mode. In the normal mode, the shutter 240 stays such that the light transmitting portion 240*b* is disposed in the optical path L1. Thus, the broad-band light beam BB is constantly incident upon the rotary filter 234.

Therefore, the three color light beams i.e. the B, G, and R light beams are sequentially produced by a turn of the rotary filter 234, and applied to the internal body portion.

In the special mode, on the other hand, the shutter 240 turns such that the light shielding portion 240*a* is disposed in the optical path L1 of the broad-band light beam BB, while the B filter 234*a* of the rotary filter 234 is disposed in the optical path L1 of the broad-band light beam BB. In other words, while the B filter 234*a* is disposed in the optical path L1, the broad-band light beam BB is shielded. In this shielding period of the broad-band light beam BB, the laser source 236*a* is turned on to supply the blue laser beam BN to the electronic endoscope 180. On the other hand, while the light transmitting portion 240*b* is disposed in the optical path L1 of the broad-band light beam BB, the blue laser beam BN is turned off, and the broad-band light beam BB propagates. In this transmitting period of the broad-band light beam BB, broad-band light beam BB transmits through the G filter 234*b* and the R filter 234*c*, so the G and R light beams are sequentially produced.

The image sensor 180*a* of the electronic endoscope 180 is a monochrome image sensor without having micro color filters in its imaging surface, in contrast to the image sensor 60 of the first embodiment. The imaging controller 70 for controlling the image sensor 180*a* performs different operation from that of the first embodiment.

Figure 23A:
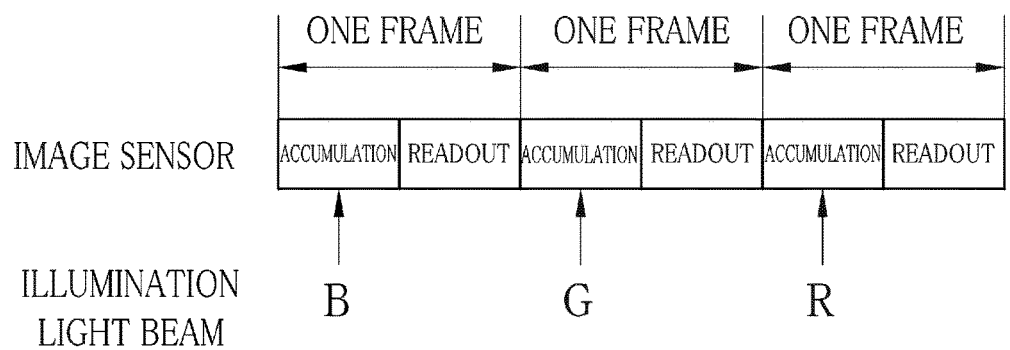
FIG. 23A is an explanatory view of imaging control in the normal mode in the case of using the light source device of FIG. 19.
Figure 23B:
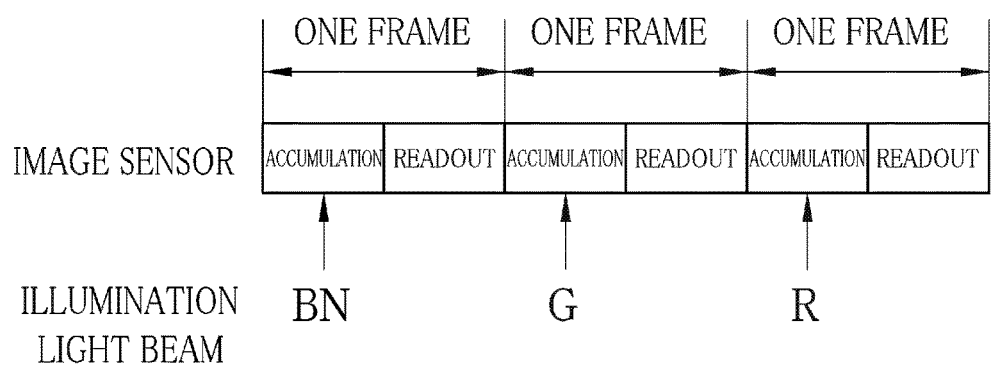
FIG. 23B is an explanatory view of imaging control in the special mode in the case of using the light source device of FIG. 19.

In the normal mode, as shown in FIG. 23A, three color image light beams of B, G, and R are captured by the frame sequential method. Each image light beam is converted into the electric charge, and frame-sequential image signals B, G, and R are produced in accordance with the accumulated electric charge. This sequential operation is repeated during the normal mode. In the special mode, on the other hand, as shown in FIG. 23B, the blue laser beam BN, the G light beam, and the R light beam are applied to the internal body portion, and three image light beams thereof are captured. Each image light beam is converted into the electric charge, and frame-sequential image signals N, G, and R are produced in accordance with the accumulated electric charge. This sequential operation is repeated during the special mode.

The normal image processor 80 produces the normal image based on the frame-sequential image signals B, G, and R. In this normal image, the frame-sequential image signal B substantially corresponds to the blue signal B1 of the first embodiment. The frame-sequential image signal G substantially corresponds to the green signal G1 of the first embodiment. The frame-sequential image signal R substantially corresponds to the red signal R1 of the first embodiment.

The special image processor 82 of the processor device 13 calculates the blood volume and the oxygen saturation level from the frame-sequential image signals N, G, and R. In this embodiment, N/G is used as a luminance ratio corresponding to the signal ratio B2/G1 of the first embodiment, and R/G is used as a luminance ratio corresponding to the signal ratio R1/G1 of the first embodiment. Accordingly, the correlation memory 85 stores the correlation among the luminance ratios N/G and R/G and the oxygen saturation level. The other steps of the operation process are the same as those of the first embodiment.

Note that, the oxygen saturation level is imaged in this embodiment, but an oxygenated hemoglobin index calculated by "blood volume (the sum of oxygenated hemoglobin and deoxygenated hemoglobin)×oxygen saturation level (%)" or a deoxygenated hemoglobin index calculated by "blood volume×(100−oxygen saturation level) (%)" may be imaged instead of or in addition to the oxygen saturation level.

Although the present invention has been fully described by the way of the preferred embodiment thereof with reference to the accompanying drawings, various changes and modifications will be apparent to those having skill in this field. Therefore, unless otherwise these changes and modifications depart from the scope of the present invention, they should be construed as included therein.

What is claimed is:

1. An endoscope system comprising:
    a light source that sequentially applies a plurality of illumination light beams having different wavelength bands to an internal body portion;
    an image sensor that sequentially captures reflected light beams from said internal body portion to obtain a plurality of frames of image signals corresponding to types of said illumination light beams;
    a processing circuitry configured for:
    calculating an oxygen saturation level of blood from said image signals;
    producing a special image that is artificially colored in accordance with said calculated oxygen saturation level;
    calculating a positional displacement in said image signals between said frames used for producing said special image, said positional displacement being caused as a result of a difference in capturing timing of said frames being obtained by sequentially applying said plurality of illumination light beams having different wavelength band to said internal body portion and sequentially capturing said reflected light beams from said internal body portion; and switching a color property of an artificial color representing said calculated oxygen saturation level in said special image in accordance with said calculated positional displacement; and a monitor that displays said special image, wherein said processing circuitry divides each of said image signals into a plurality of areas, and calculates a displacement in said image signals between said frames on an area-by-area basis as said positional displacement; and said processing circuitry determines said color property of said artificial color in each of said areas by choosing one of a plurality of color tables in accordance with said calculated positional displacement and inputting said calculated oxygen saturation level into said chosen color table, said color tables outputting a color characteristic value of an artificial color according to an oxygen saturation level being input, and said color tables being different from each other in a color characteristic value of an artificial color corresponding to same specific oxygen saturation level.

2. The endoscope system according to claim 1, wherein said processing circuitry is further configured to:

calculate as said positional displacement a displacement of an entire image in said image signals between said frames; and switch said color property of entirety of said special image in accordance with said positional displacement.

3. The endoscope system according to claim 1, wherein said processing circuitry is further configured to:

display said special image such that an amount of information of said oxygen saturation level is decreased with increase in the positional displacement.

4. The endoscope system according to claim 3, wherein the decrease in said amount of information of said oxygen saturation level is decrease in a color property value in said special image.

5. The endoscope system according to claim 4, wherein said color property value is chroma.

6. The endoscope system according to claim 1, wherein the processing circuitry is further configured to:

perform image registration in said image signals between said frames based on said positional displacement;

re-calculate said positional displacement in said image signals between said frames after said image registration; and switch said color property of said special image in accordance with said re-calculated positional displacement.

7. The endoscope system according to claim 1, wherein said processing circuitry is further configured to:

obtain a first image signal corresponding to a first illumination light beam having a first wavelength range in which a light absorption coefficient varies depending on said oxygen saturation level, a second image signal corresponding to a second illumination light beam having a second wavelength range in which said light absorption coefficient varies depending on blood volume, and a third image signal for standardizing said first and second image signals; and calculate said oxygen saturation level based on said first to third image signals.

8. The endoscope system according to claim 7, wherein said first to third wavelength ranges are within a range between 460 and 700 nm.

9. The endoscope system according to claim 7, wherein said first wavelength range is in a blue wavelength band, and said second wavelength range is in a red wavelength band.

10. A processor device of an endoscope system having a light source that sequentially applies a plurality of illumination light beams having different wavelength bands to an internal body portion, an imaging device that sequentially captures reflected light beams from said internal body portion to obtain a plurality of frames of image signals corresponding to types of said illumination light beams, and a monitor, said processor device comprising:

a processor and a memory storing a program that controls the processor to, receive said image signals from said image pickup section;

calculate an oxygen saturation level of blood from said image signals;

produce a special image that is artificially colored in accordance with said calculated oxygen saturation level;

calculate a positional displacement in said image signals between said frames used for producing said special image, said positional displacement being caused as a result of a difference in capturing timing of said frames being obtained by sequentially applying said plurality of illumination light beams having different wavelength band to said internal body portion and sequentially capturing said reflected light beams from said internal body portion;

switch a color property of an artificial color representing said calculated oxygen saturation level in said special image on said monitor in accordance with said calculated positional displacement, wherein the program further controls the processor to;

divide each of said image signals into a plurality of areas, and calculates a displacement in said image signals between said frames on an area-by-area basis as said positional displacement; and determine said color property of said artificial color in each of said areas by choosing one of a plurality of color tables in accordance with said calculated positional displacement and inputting said calculated oxygen saturation level into said chosen color table, said color tables outputting a color characteristic value of an artificial color according to an oxygen saturation level being input, and said color tables being different from each other in a color characteristic value of an artificial color corresponding to same specific oxygen saturation level.

11. A method for displaying an oxygen saturation level comprising the steps of:

sequentially applying a plurality of illumination light beams having different wavelength bands to an internal body portion;

sequentially capturing reflected light beams from said internal body portion to obtain a plurality of frames of image signals corresponding to types of said illumination light beams;

calculating an oxygen saturation level of blood from said image signals;

producing a special image, said special image being artificially colored in accordance with said calculated oxygen saturation level;

calculating a positional displacement in said image signals between said frames used for producing said special image, said positional displacement being caused as a result of a difference in capturing timing of said frames being obtained by sequentially applying said plurality of illumination light beams having different wavelength band to said internal body portion and sequentially capturing said reflected light beams from said internal body portion;

switching a color property of an artificial color representing said calculated oxygen saturation level in said special image on a monitor in accordance with said calculated displacement;

dividing each of said image signals into a plurality of areas, and calculating a displacement in said image signals between said frames on an area-by-area basis as said positional displacement; and determining said color property of said artificial color in each of said areas by choosing one of a plurality of color tables in accordance with said positional displacement and inputting said calculated oxygen saturation level into said chosen color table, said color tables outputting a color characteristic value of an artificial color according to an oxygen saturation level being input, and said color tables being different from each other in a color characteristic value of an artificial color corresponding to same specific oxygen saturation level.

* * * * *